US008990135B2

(12) United States Patent
Syed et al.

(10) Patent No.: US 8,990,135 B2
(45) Date of Patent: Mar. 24, 2015

(54) PERSONALIZED HEALTH RISK ASSESSMENT FOR CRITICAL CARE

(75) Inventors: Zeeshan H. Syed, Ann Arbor, MI (US); Ilan S. Rubinfeld, Ann Arbor, MI (US)

(73) Assignees: The Regents of the University of Michigan, Ann Arbor, MI (US); Henry Ford Health System, Detroit, MI (US)

( * ) Notice: Subject to any disclaimer, the term of this patent is extended or adjusted under 35 U.S.C. 154(b) by 401 days.

(21) Appl. No.: 13/253,928

(22) Filed: Oct. 5, 2011

(65) Prior Publication Data

US 2012/0059779 A1 Mar. 8, 2012

Related U.S. Application Data

(63) Continuation-in-part of application No. 13/161,088, filed on Jun. 15, 2011, now Pat. No. 8,914,319.

(60) Provisional application No. 61/355,128, filed on Jun. 15, 2010.

(51) Int. Cl.
*G06N 5/00* (2006.01)
*G06F 17/00* (2006.01)
*G06F 19/00* (2011.01)
*G06N 99/00* (2010.01)

(52) U.S. Cl.
CPC .......... *G06F 19/3431* (2013.01); *G06N 99/005* (2013.01); *G06F 19/3437* (2013.01); *G06F 19/3443* (2013.01); *Y10S 706/924* (2013.01)
USPC .......................................... 706/45; 706/924

(58) Field of Classification Search
USPC .................................................. 706/45, 924
See application file for complete search history.

(56) References Cited

U.S. PATENT DOCUMENTS

| | | |
|---|---|---|
| 5,862,304 A | 1/1999 | Ravdin et al. |
| 7,076,288 B2 | 7/2006 | Skinner |
| 7,617,078 B2 | 11/2009 | Rao et al. |
| 7,702,598 B2 | 4/2010 | Saidi et al. |
| 8,468,104 B1 | 6/2013 | Chelian et al. |
| 8,544,087 B1 | 9/2013 | Eskin et al. |
| 2005/0203773 A1 | 9/2005 | Soto et al. |
| 2006/0230006 A1 | 10/2006 | Buscema |

(Continued)

OTHER PUBLICATIONS

Cohen, M.E. et al. "Development of an American College of Surgeons National Surgery Quality Improvement Program: morbidity and mortality risk calculator for colorectal surgery." Journal of the American College of Surgeons 208.6 (2009): pp. 1009-1016. DOI: 10.1016/j.jamcollsurg.2009.01.043.*

(Continued)

*Primary Examiner* — Lut Wong
*Assistant Examiner* — Benjamin Buss
(74) *Attorney, Agent, or Firm* — Marshall, Gerstein & Borun LLP

(57) ABSTRACT

A method for assessing whether a patient is at risk of developing a clinical condition includes receiving training data representing a set of patient-related variables for each of a plurality of patients; generating model data based on the received training data; receiving target data representing the set of patient-related variables for a target patient; determining a risk level for the target patient of developing the clinical condition; and indicating the risk level of the target patient, where the set of patient-related variables consists of a first set of variables when the clinical condition is a mortality condition and a second set of variables when the clinical condition is a morbidity condition.

13 Claims, 10 Drawing Sheets

(56) References Cited

U.S. PATENT DOCUMENTS

| | | |
|---|---|---|
| 2007/0286470 A1 | 12/2007 | Bernard et al. |
| 2007/0289013 A1 | 12/2007 | Lim |
| 2008/0025592 A1 | 1/2008 | Jerebko et al. |
| 2008/0201278 A1 | 8/2008 | Muller et al. |
| 2009/0080752 A1 | 3/2009 | Ruth et al. |
| 2009/0192394 A1 | 7/2009 | Guttag et al. |
| 2009/0297002 A1 | 12/2009 | Zhang et al. |
| 2010/0063948 A1 | 3/2010 | Virkar et al. |
| 2011/0125680 A1 | 5/2011 | Bosworth et al. |
| 2011/0212447 A1* | 9/2011 | Donlon et al. ............... 435/6.11 |
| 2013/0035951 A1* | 2/2013 | Frey .............................. 600/300 |

OTHER PUBLICATIONS

Gibbs, J. et al. "Preoperative serum albumin level as a predictor of operative mortality and morbidity: results from the National VA Surgical Risk Study." Archives of Surgery 134.1 (1999): 36-42. DOI: 10.1001/archsurg.134.1.36.*

Longo, W.E. et al. "Risk factors for morbidity and mortality after colectomy for colon cancer." Diseases of the colon & rectum 43.1 (2000): 83-91.*

Wright, C.D. et al. "Predictors of major morbidity and mortality after esophagectomy for esophageal cancer: a Society of Thoracic Surgeons General Thoracic Surgery Database risk adjustment model." The Journal of thoracic and cardiovascular surgery 137.3 (2009): 587-596. DOI: 10.1016/j.jtcvs.2008.11.042.*

International Preliminary Report on Patentability for Application No. PCT/US2011/024469 dated Aug. 23, 2012, 6 pages.

"A Probabilistic Resource Allocating Network for Novelty Detection", Roberts et al., Neural Computation 6(2), pp. 270-284, 1994.

"Novelty Detection for the Identification of Masses in Mammograms", Tarassenko et al., Artificial Neural Networks, Fourth International Conference, pp. 442-447, 1995.

"Informal Identification of Outliers in Medical Data", Laurikkala et al., 5th International Workshop on Intelligent Data Analysis in Medicine and Pharmacology, Berlin, Germany, 5 pages, 2000.

"A Linear Programming Approach to Novelty Detection", Campbell et al., Advances in Neural Information Processing Systems, pp. 395-401, 2001.

"Evidence-based Anomaly Detection in Clinical Domains", Hauskrecht et al., AMIA Annual Symposium Proceedings, American Medical Informatics Association, pp. 319-323, 2007.

"Unsupervised Risk Stratification in Clinical Datasets" Identifying Patients at Risk of Rare Outcomes, Syed et al., Proceedings of the 27th International Conference on Machine Learning, Haifa, Israel, 8 pages, Jun. 23, 2010.

"Fast Anomaly Detection in Dynamic Clinical Datasets Using Near-Optimal Hashing With Concentric Expansions", Syed et al., IEEE International Conference on Data Mining: Workshop, pp. 763-770, Sydney, Australia, Dec. 13, 2010.

"Identifying High-Risk Patients Without Labeled Training Data: Anomaly Detection Methodologies to Predict Adverse Outcomes", Syed et al., American Medical Informatics Association Annual Symposium, pp. 772-776, Washington, D.C., Nov. 15, 2010.

"Predicting Surgical Risk: How Much Data is Enough?", Rubinfeld et al., AMIA Annual Symposium Proceedings 2010, pp. 777-781, Published online Nov. 13, 2010.

"Using Procedural Codes to Supplement Risk Adjustment: A Nonparametric Learning Approach", Syed et al., Journal of the American College of Surgeons, vol. 212, Issue 6, pp. 1086-1093.e1, Jun. 2011.

Yamanishi et al., "Discovering Outlier Filtering Rules From Unlabeled Data: Combining a Supervised Learner With an Unsupervised Learner", Proceedings of the Seventh ACM SIGKDD International Conference on Knowledge Discovery and Data Mining, ACM, 2011.

Shon et al., "A Hybrid Machine Learning Approach to Network Anomaly Detection", Information Sciences 177.18, 2007, pp. 3799-3821.

Dasgupta et al., "Anomaly Detection in Multidimensional Data Using Negative Selection Algorithm", Evolutionary Computation, CEC'02, Proceedings of the 2002 Congress, vol. 2, IEEE 2002.

Fine et al., "A Prediction Rule to identify Low-Risk Patients With Community-Acquired Pneumonia", New England Journal of Medicine 336.4, 1997, pp. 243-250.

Liu et al., "An Investigation of Practical Approximate Nearest Neighbor Algorithms", Advances in Neural Information Processing Systems, 2004, pp. 825-832.

Chandola et al., "Anomaly Detection: A Survey", ACM Computing Surveys (CSUR), 41(3), 2009, p. 15.

Suzuki et al., "Detecting Interesting Exceptions From Medical Test Data With Visual Summarization", Data Mining, ICDM, Third IEEE International Conference on IEEE, 2003.

Hauskrecht et al., "Evidence-Based Anomaly Detection in Clinical Domains", AMIA Annual Symposium Proceedings, American Medical Informatics Association, vol. 2007, p. 319.

Roberts, "Extreme Value Statistics for Novelty Detection in Biomedical Data Processing", Science, Measurement and Technology, IEEE Proceedings, vol. 147, No. 6, Nov. 2000, pp. 363-367.

Office Action in U.S. Appl. No. 13/161,088 dated Aug. 1, 2013.

Office Action in U.S. Appl. No. 13/161,088 dated Feb. 12, 2014.

Office Action in U.S. Appl. No. 13/161,088 dated Jul. 2, 2014.

\* cited by examiner

PERSONALIZED HEALTH RISK ASSESSMENT FOR CRITICAL CARE

CROSS-REFERENCE TO RELATED APPLICATIONS

The present application is a continuation-in-part of U.S. patent application Ser. No. 13/161,088 filed Jun. 15, 2011 (issued as U.S. Pat. No. 8,914,319), which claims the benefit of U.S. Provisional Patent Application No. 61/355,128 filed Jun. 15, 2010. Each of the above applications is incorporated herein by reference in its entirety for all purposes.

TECHNICAL FIELD

The present application relates generally to health risk assessments and, more specifically, to a method and system for providing personalized assessments of patient risk for adverse outcomes.

BACKGROUND

Patients in a critical care setting are often subject to a significant risk of experiencing adverse outcomes, such as death, stroke, sepsis, coma, wound infection, or other undesired clinical conditions. The ability to precisely assess the risk of an adverse outcome can help to improve the quality of care delivered to these patients by identifying those who are at a significantly increased or decreased risk and then treating or monitoring those patients accordingly. Patients may also welcome having precise estimates of risk available to them for use in discussions with their healthcare providers. A precise assessment of risk may also be utilized for other purposes, such as an acuity adjustment of data.

Health risk assessment systems generally use data from a patient population as "training data" so that the systems can learn how to assess the health risks of a particular patient. The sheer volume of information that has traditionally been collected and analyzed for each patient in the population, however, poses a serious challenge to health care professionals. Caregivers often must keep track of a large variety of patient data, including for example demographics, comorbidities, laboratory results, imaging results, parameters for continuous monitoring, and a record of interventions. While recent advances allow these variables to be combined (for many clinical applications) into models with excellent risk adjustment and prediction, the collection processes for these variables increase health care costs and impose demands on both caregivers and patients. Laboratory data may be particularly invasive, costly and time-intensive to obtain. Moreover, certain types of data relating to a patient population, such as surgical and diagnostic codes, may not be amenable to certain risk prediction techniques despite containing useful information.

DETAILED DESCRIPTION

The disclosed system utilizes anomaly detection methods and variations thereof to assess the risk of an adverse outcome. Although anomaly detection methods allow unsupervised learning and do not require positively and negatively labeled training data, they still can provide a useful prediction of risk. This predictive ability of anomaly detection methods supports the hypothesis that patients who differ the most from other patients in a population, in any direction, are likely to be at an increased risk of an adverse outcome.

These qualities of anomaly detection methods make them useful for predicting adverse outcomes that are rare, where a given population is unlikely to include a sufficient number of positive training samples. In some instances, anomaly detection methods used as risk indicators can even outperform conventional, supervised learning methods that do require positively and negatively labeled training data. This result is believed to be due to the fact that supervised learning methods may be unable to generalize for complex, multi-factorial adverse outcomes when only a small number of patients in a large training population experience those adverse outcomes.

Anomaly detection methods can also advantageously provide a uniform approach to identifying patient risk for many different types of clinical conditions. Conversely, classification-based, supervised learning methods making use of positive and negative labels typically require constructing a separate model for each clinical condition for which risk is being assessed.

Examples of anomaly detection methods include minimum enclosing ball (MEB), 1-class support vector machine (1-class SVM), k-nearest neighbor (k-NN) and cluster-based methods. Each of these exemplary methods is discussed in more detail below. Also discussed below is a variant of the k-NN approach that can reduce computational complexity and may be particularly useful for large and/or dynamically changing datasets, and a multi-task learning method that incorporates certain advantages of anomaly detection methods. The disclosed system encompasses these methods, variations of these methods, and other methods not specifically discussed herein.

Anomaly Detection Methods

Figure 1:
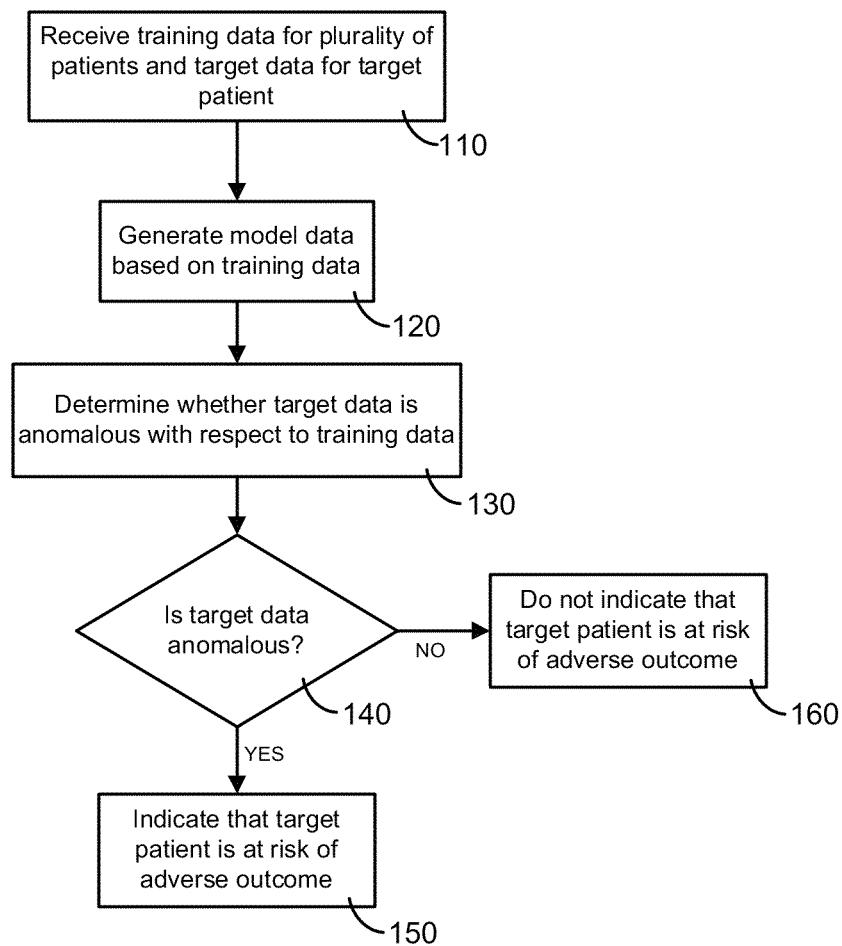
FIG. 1 illustrates an exemplary block diagram of a method for assessing the risk of an adverse outcome using anomaly detection.

FIG. 1 illustrates an exemplary block diagram of a method 100 for assessing the risk of an adverse outcome using anomaly detection. The adverse outcome for which risk is being assessed may correspond to a clinical condition such as death, stroke, sepsis, coma, or wound infection, for example. In some embodiments, the adverse outcome may correspond to multiple clinical conditions, where the assessed risk may represent the risk of developing one or more of the multiple clinical conditions.

The method 100 may receive training data for a plurality of patients and target data for a target patient (block 110). The training data may include data relating to a variety of factors for each of the patients in the training sample, such as demographics (e.g., gender, age), comorbidity (e.g., presence of a particular disease), laboratory results (e.g., creatinine level, albumin level) and/or procedural factors (e.g., type of surgical procedure performed on a patient, amount of work done by a surgeon on a patient), for example. Although the method 100 does not generally require that training data include label data indicating whether each of the plurality of patients is positively associated with the adverse outcome, the training data may or may not include such label data. In some embodiments, the training data may lack label data because the outcomes (e.g., 30-day mortality or morbidity outcomes) for some or all of the plurality of patients have not yet occurred and therefore cannot yet be known. The target data corresponds to the patient whose risk is being assessed (i.e., the target patient), and may include data relating to some or all of the factors to which the training data relates.

In some embodiments, the method 100 may utilize the target patient's data in addition to other patients' data for training of the predictive system. Thus, the target data may itself be a part of the training data. In other embodiments, the target data may not be used for training, in which case the target data may not be part of the training data. In some embodiments, the target data may be received when the training data is received. In other embodiments, the target data may be received at an earlier or later time. In some embodiments, either or both of the target data and the training data may be received in a single stream of data. In other embodiments, either or both of the target data and the training data may be received piecemeal over an extended period of time.

The method 100 may generate model data based on the training data (block 120). The model data may be generated according to an anomaly detection method. As discussed below, specific anomaly detection methods are employed in the embodiments of the methods illustrated in FIGS. 2 and 3. In some embodiments, the generation of model data may involve using the received training data to solve for certain parameters associated with a higher-level representation of the training data. As discussed in more detail in connection with FIG. 2, for example, an MEB method may generate model data by using training data to solve for the center and radius of a minimum volume hypersphere that encloses the training data. For certain other anomaly detection methods, however, the generation of model data may consist of an action that does not transform the training data to a higher-level representation, such as directly accessing the training data for use in the calculations (block 130, discussed below) that determine whether the target data is anomalous. For example, the k-NN method discussed in connection with FIG. 3 is a purely data-driven method wherein the generated model data is the training data itself.

The method 100 may determine whether the target data associated with the target patient is anomalous with respect to the received training data (block 130). This determination may be made at least in part by performing one or more calculations involving the received target data and the generated model data. Specific examples of how this determination may be made are described in connection with the embodiments illustrated in the methods of FIGS. 2 and 3.

If the target data is determined to be anomalous with respect to the training data (block 140), the method 100 may indicate that the target patient is at risk of an adverse outcome (block 150). In some embodiments, the method 100 may indicate that a target patient is at risk of an adverse outcome by setting the value of a data field representing patient risk. In some embodiments, the method 100 may indicate that a target patient is at risk of an adverse outcome by generating or providing a report. In some embodiments, the method 100 may indicate that a target patient is at risk of an adverse outcome by generating or providing an input to another system or program, such as an acuity adjustment system or program. If the target data is not determined to be anomalous with respect to the training data (block 140), the method 100 may not indicate that the target patient is at risk of an adverse outcome (block 160). As noted above, the adverse outcome may represent a single clinical condition in some embodiments, and in some embodiments may represent multiple clinical conditions where the assessed risk is the risk of developing one or more of those clinical conditions.

Although the method 100 of FIG. 1 depicts a binary determination of whether the target data is anomalous (block 130), the method 100 may additionally (or alternatively) calculate an anomaly score for the target data that is continuous or has more than two discrete values. Like the binary determination of block 130, the anomaly score may be based on one or more calculations involving the target data and the model data. If an anomaly score is calculated, the method 100 may then additionally (or alternatively) indicate the extent to which the target patient is at risk of the adverse outcome.

Moreover, although the method 100 generally does not require that training data be positively or negatively labeled, some additional predictive precision may be obtained if the system is trained based only on negative examples, i.e., if the generation of model data (block 120) is based only on training data for patients known to be free of the clinical condition(s) associated with the adverse outcome. If training data is positively and negatively labeled, for example, then in some embodiments the method 100 may achieve this by determining that portions of the training data correspond to patients positively associated with the adverse outcome, and disregarding those portions of the training data so that they are not used to generate the model data.

Figure 2:
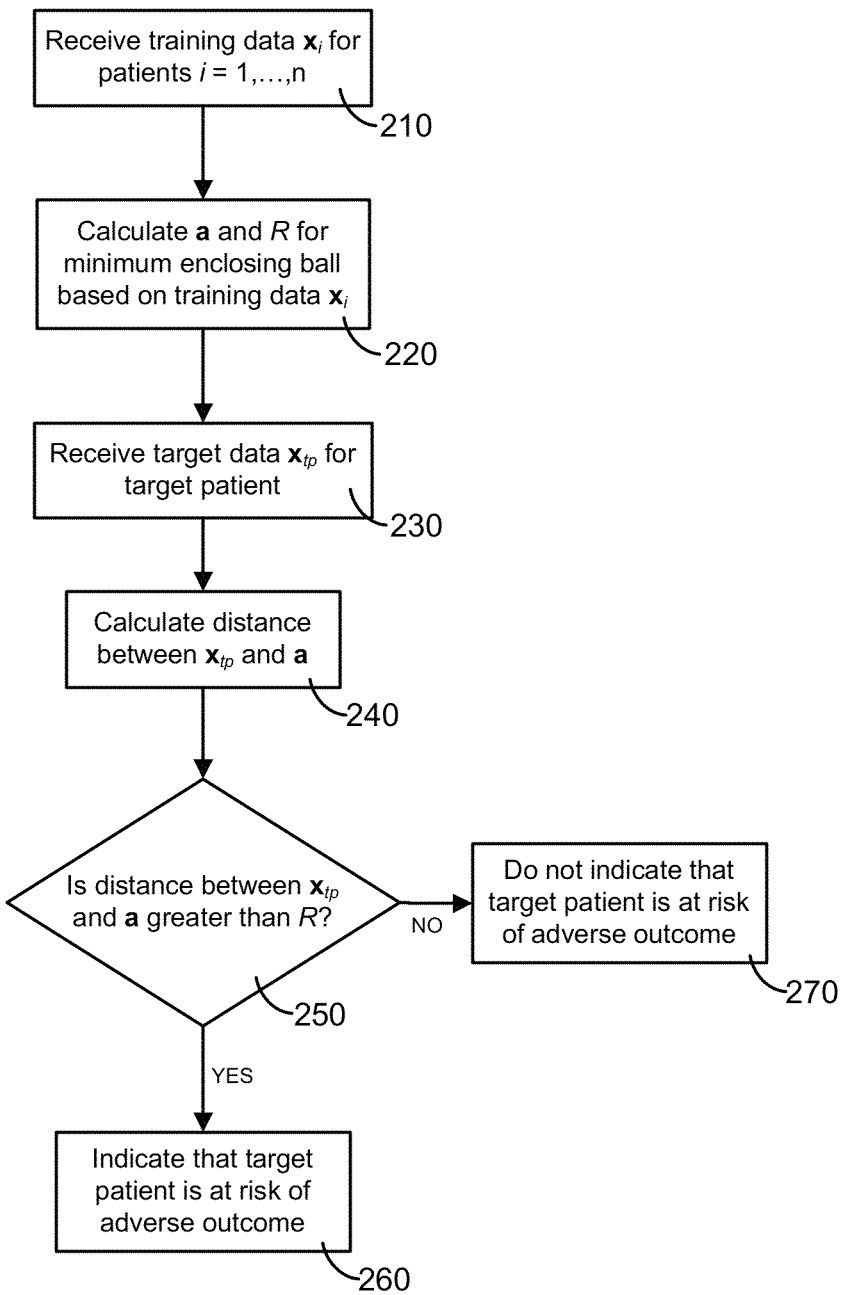
FIG. 2 illustrates an exemplary block diagram of a method for assessing the risk of an adverse outcome using an MEB method for anomaly detection.
Figure 3:
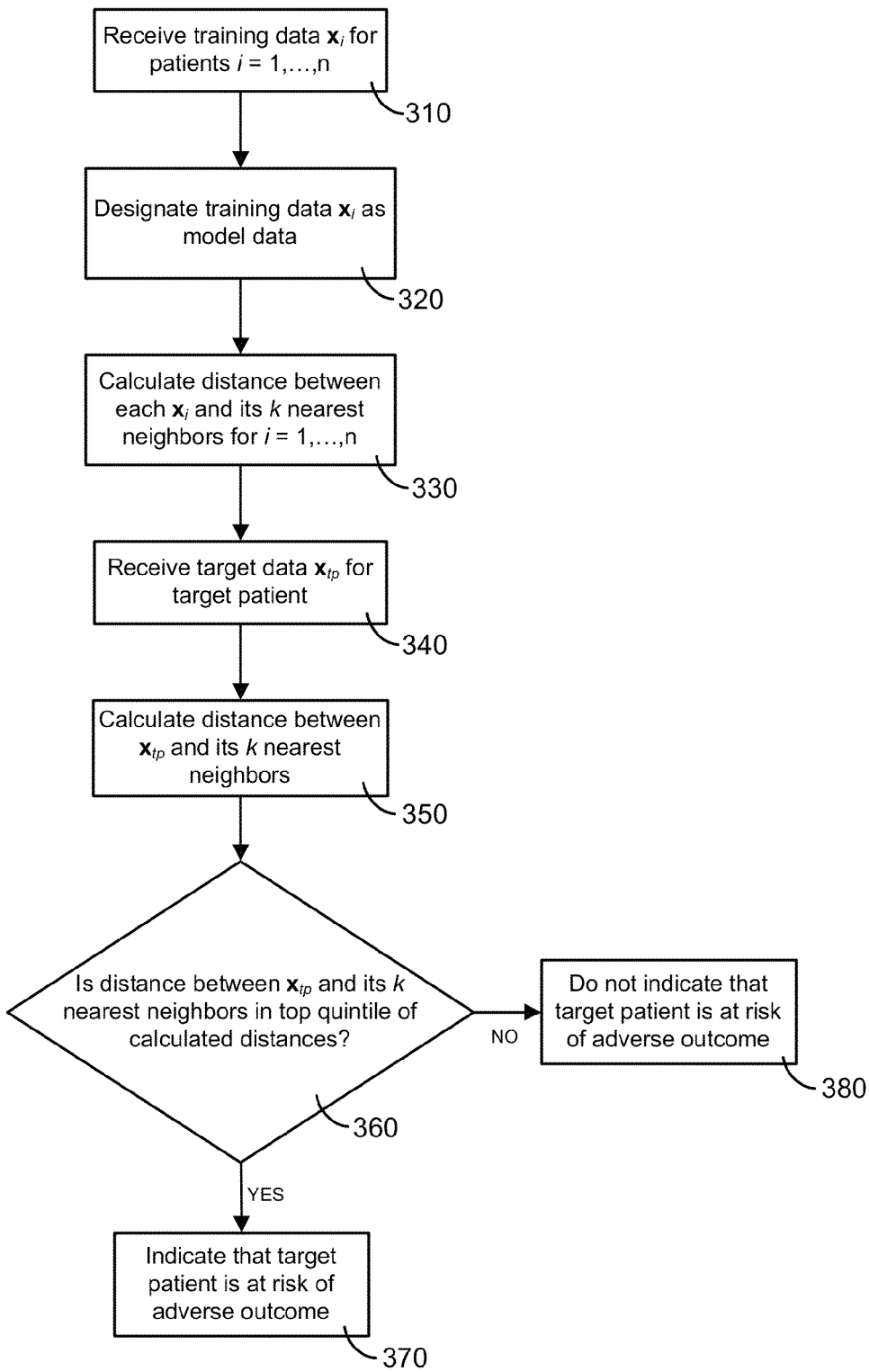
FIG. 3 illustrates an exemplary block diagram of a method for assessing the risk of an adverse outcome using a k-NN method for anomaly detection.

FIG. 2 illustrates an exemplary block diagram of a method 200 for assessing the risk of an adverse outcome using an MEB method for anomaly detection. As with the method 100 illustrated in FIG. 1, the adverse outcome may correspond to a single clinical condition or to multiple clinical conditions.

The method 200 may receive training data $x_i$ for patients $i=1, \ldots, n$ (block 210). In some embodiments, each $x_i$ may be a multidimensional vector having one dimension for each feature taken into account (e.g., age, weight, preoperative albumin level, etc.). Although the method 200 does not generally require that training data include label data that indicates whether each of the plurality of patients is positively associated with the adverse outcome, the training data $x_i$ may or may not include such label data. In some embodiments, the training data $x_i$ may lack label data because the outcomes (e.g., 30-day mortality or morbidity outcomes) for some or all of the patients $i=1, \ldots, n$ have not yet occurred and therefore cannot yet be known.

Based on the training data $x_i$, the method 200 may calculate model data that includes the center a and radius R for a hypersphere according to the MEB method (block 220). This task can be formulated as minimizing the error function:

$$F(R, a, \xi_i) = R^2 + C \sum_i \xi_i \quad (1)$$

over R, a, $\xi_i$ subject to the constraints:

$$\|x_i - a\|^2 \leq R^2 + \xi_i, \xi_i \geq 0, \forall i \quad (2)$$

where a is the center and R is the radius of the minimum enclosing ball. The slack variables $\xi_i \geq 0$ account for errors corresponding to outliers in the data that do not fit within the radius R of the minimum enclosing ball. The parameter C controls the trade-off between the volume of the minimum enclosing ball and the number of errors.

The dual of the MEB problem is given by:

$$L(R, a, \alpha_i, \gamma_i, \xi_i) = R^2 + C \sum_i \xi_i + \sum_i \alpha_i (\|x_i\|^2 - 2a \cdot x_i + \|a\|^2) - \sum_i \alpha_i (R^2 + \xi_i) - \sum_i \gamma_i \xi_i \quad (3)$$

where $\alpha_i \geq 0$ and $\gamma_i \geq 0$ correspond to the Lagrange multipliers. L is minimized with respect to R, a, $\xi_i$ and maximized with respect to $\alpha_i$ and $\gamma_i$. This can be simplified to:

$$L = \sum_i \alpha_i (x_i \cdot x_i) - \sum_{i,j} \alpha_i \alpha_j (x_i \cdot x_j) \quad (4)$$

subject to the constraints:

$$0 \leq \alpha_i \leq C \quad (5)$$

The inner products in Equation 4 can be replaced by a kernel function to obtain a more flexible data description than a rigid hypersphere. Some embodiments may use the Gaussian kernel function $K(x_i, x_j) = \exp(-\|x_i - x_j\|^2 / 2s^2)$, which is independent of the position of the dataset with respect to the origin and only depends on the distances between objects.

The method 200 may receive target data $x_{tp}$ for a target patient (block 230). While FIG. 2 depicts this as a step occurring after the steps of receiving the training data $x_i$ and calculating the model data a and R, the target data $x_{tp}$ may in some embodiments be received prior to, between, or contemporaneously with any of those steps, and may or may not be a part of the training data $x_i$ used to calculate the model data a and R.

The method 200 may calculate the distance between the target data $x_{tp}$ and the calculated parameter a (block 240), i.e., the distance between the target data $x_{tp}$ and the center of the hypersphere. The method 200 may then compare the calculated distance to the calculated parameter R, i.e., to the radius of the hypersphere. If the distance is greater than R (block 250), the method 200 may indicate that the target patient is at risk of the adverse outcome (block 260). In some embodiments, the method 200 may indicate that a target patient is at risk of an adverse outcome by setting the value of a data field representing patient risk. In some embodiments, the method 200 may indicate that a target patient is at risk of an adverse outcome by generating or providing a report. In some embodiments, the method 200 may indicate that a target patient is at risk of an adverse outcome by generating or providing an input to another system or program, such as an acuity adjustment system or program. If the distance is not greater than R, the method 200 may not indicate that the target patient is at risk of the adverse outcome (block 270).

Calculations for the distance between $x_{tp}$ and a (block 240) and its comparison with R (block 250) may be represented as follows:

$$\|x_k - a\| = (x_k \cdot x_k) - 2 \sum_i \alpha_i (x_k \cdot x_i) + \sum_{i,j} \alpha_i \alpha_j (x_i \cdot x_j) > R^2 \quad (6)$$

In some embodiments, the inner product of Equation 6 may be replaced with the Gaussian kernel function described above, which leads to the following formulation of the calculation and comparison performed by the method 200 at blocks 240 and 250:

$$\sum_i \alpha_i \exp\left(\frac{-\|x_k - x_i\|^2}{2s^2}\right) \geq -R^2/2 + C \quad (7)$$

As discussed above in connection with the method 100 illustrated in FIG. 1, the method 200 may additionally (or alternatively) calculate an anomaly score for the target data that is continuous or has more than two discrete values. In some embodiments, for example, the quantity on the left side of Equation 7 above may be used as an anomaly score. If an anomaly score is calculated, the method 200 may then additionally (or alternatively) indicate the extent to which the target patient is at risk of the adverse outcome.

Moreover, although the method 200 generally does not require that training data be positively or negatively labeled, some additional predictive precision may be obtained if the system is trained based only on negative examples, i.e., if the generation of model data (block 220) is based only on training data for patients known to be free of the clinical condition(s) associated with the adverse outcome. If training data is positively and negatively labeled, for example, then in some embodiments the method 200 can achieve this by determining that portions of the training data correspond to patients positively associated with the adverse outcome, and disregarding those portions of the training data so that they are not used to generate the model data.

FIG. 3 illustrates an exemplary block diagram of a method 300 for assessing the risk of an adverse outcome using a k-NN method for anomaly detection. As with the method 100 illustrated in FIG. 1, the adverse outcome may correspond to a single clinical condition or to multiple clinical conditions.

The method 300 may receive training data $x_i$ for patients i=1, . . . , n (block 310). In some embodiments, each $x_i$ may be a multidimensional vector having one dimension for each feature taken into account (e.g., age, weight, preoperative albumin level, etc.). Although the method 300 does not generally require that training data include label data that indicates whether each of the plurality of patients is positively associated with the adverse outcome, the training data $x_i$ may or may not include such label data. In some embodiments, the training data $x_i$ may lack label data because the outcomes (e.g., 30-day mortality or morbidity outcomes) for some or all of the patients i=1, . . . , n have not yet occurred and therefore cannot yet be known.

Unlike the MEB method employed in the method 200 illustrated in FIG. 2, the k-NN method does not need to transform the training data $x_i$ to a higher-level representation. Thus, the method 300 may generate model data simply by designating the training data $x_i$ as the model data (block 320), for example. In some embodiments, model data may be generated merely by retrieving the training data $x_i$ for use in the distance calculations (block 350, discussed below) involving $x_{tp}$ and $x_i$.

The method 300 may calculate the distance between each $x_i$ (for i=1, . . . , n) of the training data and its k nearest neighbors (block 330), where k may be a predetermined integer value. This set of calculated distances may be utilized later in the method 300, when the comparison is made to determine whether the target data $x_{tp}$ is anomalous (block 360).

The method 300 may receive target data $x_{tp}$ for a target patient (block 340). While FIG. 3 depicts this as a step occurring after the steps of receiving the training data $x_i$, designating $x_i$ as the model data, and calculating the distance between each $x_i$ and its k nearest neighbors, the target data $x_{tp}$ may in some embodiments be received prior to, between, or contemporaneously with any of those steps, and may or may not be a part of the training data $x_i$ that is designated as the model data.

The method 300 may calculate the distance between the target data $x_{tp}$ of the target patient and its k-nearest neighbors (block 350). Because the training data $x_i$ may be designated as the model data, this calculation may involve calculating the distance between the target data $x_{tp}$ and the k-nearest neighbors from the training data $x_i$.

If the calculated distance for $x_{tp}$ is in the top quintile of the distances for the patient population calculated at block 330 (block 360), the method 300 may indicate that the target patient is at risk of the adverse outcome (block 370). In some embodiments, the method 300 may indicate that a target patient is at risk of an adverse outcome by setting the value of a data field representing patient risk. In some embodiments, the method 300 may indicate that a target patient is at risk of an adverse outcome by generating or providing a report. In some embodiments, the method 300 may indicate that a target patient is at risk of an adverse outcome by generating or providing an input to another system or program, such as an acuity adjustment system or program. If the calculated distance for $x_{tp}$ is not in the top quintile of distances for the patient population at block 330 (block 360), the method 300 may not indicate that the target patient is at risk of the adverse outcome (block 380). In some embodiments, the method 300 may use a different threshold (other than the top quintile) for determining whether the calculated distance between the target data $x_{tp}$ and its k-nearest neighbors corresponds to the target patient being at risk of an adverse outcome.

Although the method 300 generally does not require that training data be positively or negatively labeled, some additional predictive precision may be obtained if the system is trained based only on negative examples, i.e., if the generation of model data (block 320) is based only on training data for patients known to be free of the clinical condition(s) associated with the adverse outcome. If training data is positively and negatively labeled, for example, then in some embodiments the method 300 can achieve this by determining that portions of the training data correspond to patients positively associated with the adverse outcome, and disregarding those portions of the training data so that they are not used to generate the model data.

Other embodiments may utilize different anomaly detection methods. For example, some embodiments may use "classification-based" anomaly detection, such as a 1-class SVM method. Given the normalized feature vectors $x_i$ for patients i=1, . . . , n, the 1-class SVM method maps the data into a second feature space F using a feature map $\phi$. Dot products in F can be computed using a simple kernel $k(x_i, x_j) = (\phi)(x_i) \cdot \phi(x_j)$, such as the radial basis function (RBF) kernel $k(x_i, x_j) = \exp(-\gamma(\|x_i - x_j\|^2))$.

In contrast to a 2-class SVM algorithm, which separates two classes in the feature space F by a hyperplane, the 1-class SVM attempts to separate the entire dataset from the origin. This is done by solving the following quadratic problem (which penalizes feature vectors not separated from the origin, while simultaneously trying to maximize the distance of this hyperplane from the origin):

$$\min_{\omega,\xi,p} \frac{1}{2}\|\omega\|^2 + \frac{1}{vn}\sum_i \xi_i - p \qquad (8)$$

subject to:

$$(\omega \cdot \Phi(z_i)) \geq p - \xi_i, i=1,\ldots,n\; \xi_i \geq 0 \qquad (9)$$

where v reflects the tradeoff between incorporating outliers and minimizing the support region size.

The resulting decision function, in terms of the Lagrange multipliers is then:

$$f(x) = \mathrm{sgn}\left(\sum_i \alpha_i k(x_i, x) - p\right) \qquad (10)$$

Anomalies in a population may be detected by first developing a 1-class SVM on the data for all patients, and then using the resulting decision function to identify patients with feature vectors that are not separated from the hyperplane. These patients, who lie outside the enclosing boundary, are labeled as anomalies. The parameter v can be varied during the process of developing the 1-class SVM to control the size of this group.

As another example, some embodiments may use "cluster-based" anomaly detection. For each feature vector $x_i$, $N(x_i)$ may be defined to be the number of points within W of $x_i$:

$$N(x_i) = |\{s|(x_i - s)^2 \leq W\}| \qquad (11)$$

These values can be used to estimate how many points are "near" each point in the feature space. Patients with low values may be identified as anomalies.

A fixed width clustering algorithm may be used to approximate $N(x_i)$ in a computationally efficient manner for all i=1, . . . , n. This algorithm may set the first point as the center of the first cluster. Every subsequent point that is within W of this point is added to the cluster, or is otherwise set to be a new cluster. Some points may be added to multiple clusters using this approach. At the end of this process, $N(x_i)$ may be approximated by the number of points in the cluster to which $x_i$ belongs.

Fast Anomaly Detection in Dynamic Clinical Datasets

The k-NN method described above in connection with FIG. 3 has certain advantageous qualities. First, it is non-parametric and does not make any assumptions regarding the generative distribution for the data. Instead, it is a purely data-driven method. This makes it appropriate for capturing complex cases. Second, it is generally robust to noise because the likelihood that an anomaly will form a close neighborhood in the dataset is low. Despite these advantages, a notable limitation of unsupervised anomaly detection using the k-NN method is the computational complexity of the approach. Finding the nearest neighbors of a patient may involve computing the distance to all other patients in the dataset.

To reduce the computational complexity, some embodiments may use a modified version of the k-NN method. Several variations of the basic k-NN algorithm can improve its efficiency. Spatial index structures (e.g., KD-trees, R-trees, or X-trees) work well for low-dimensional data, but they suffer from the curse of dimensionality and are worse than the basic k-NN algorithm when the data has as few as 10 or 20 features. Methods to partition the feature space (e.g., into hyper-rectangles) are also similarly affected by the high dimensionality and are exponential in the number of dimensions. Pruning sufficiently randomized data to reduce average complexity may also improve efficiency of the basic k-NN algorithm. This approach iteratively calculates the nearest neighbors for a data instance and sets the anomaly threshold to the score of the weakest anomaly found in a working group of size n. Using this pruning procedure, the algorithm discards instances that are close and therefore not interesting. While the worst case complexity of this approach is still quadratic, it achieves a near-linear runtime on different datasets. An analogous technique first clusters the data, and then computes lower and upper bounds on the distances of instances from their k nearest neighbors in each partition. This information is used to identify partitions that cannot possibly contain the top n anomalies. Anomalies are then computed from the remaining instances in a final phase. A further variant of these methods uses recursive binning and re-projection based on divisive hierarchical clustering, which iteratively partitions the data into k partitions for a fixed number of iterations and scans through each bin to find anomalies. This approach achieves a quadratic worst case running time and a log-linear average computational complexity.

While these methods may provide substantial improvements over the basic k-NN algorithm for anomaly detection, they focus on the batch discovery of anomalies. These methods are not directly applicable to the situation where the data is dynamically changing. For clinical datasets that are dynamically changing, where patients are continuously being added to or removed from populations, and/or where populations are changing as a function of time due to technological advances, an alternate approach may be preferable. For example, some embodiments may rapidly identify anomalies in clinical datasets using the ideas of both pruning and randomization. One such method may find an approximate solution to the k-NN method using locality sensitive hashing (LSH) based on p-stable distributions. The method may be optimized to use multiple LSH searches, each with a geometrically increasing radius, to find the k-nearest neighbors of patients in a dataset. Such an approach may significantly improve runtime over the exact k-NN algorithm, and may be appropriate for large, high-dimensional datasets that are dynamically changing.

In the context of dynamically changing datasets, the approach may quickly resolve individual queries that require patients to be compared to a dataset and assigned an anomaly score based on the k-nearest neighbors found. These queries may be due to new patients entering the patient population, or due to changes in the states of patients already in the population. The focus on improving speed of these individual queries is different from the goal of mining a batch of data to find anomalies. In particular, unlike the batch discovery of anomalies, where the computation performed while assessing one data point might be used to reduce the time needed to assess other points, the approach treats each new query as an independent request. In addition to providing rapid responses to queries (i.e., to allow for large populations or for cases where patient state is changing quickly), the approach may also be advantageous for handling deletions (or modifications corresponding to deletions and re-insertions) for cases where patients are leaving the population or changing substantially over time.

LSH can be used to efficiently discover matches within a distance R of a query. The amount of work carried out by LSH depends on this choice of R. It is important to note that LSH is optimized to find points within a given radius R, rather than a given number of closest matches k. By contrast, the goal for the modified k-NN approach described here is to find the k closest matches to a query. This lack of parameterization by R is an important distinction that allows the use of an approach where R is varied in a computationally efficient manner to find the k-nearest matches.

The key idea of LSH is to hash data points using several hash functions with the property that for each function, the probability of collision is much higher for objects that are close to each other than for those that are far apart. This allows for the efficient discovery of nearest neighbors by hashing a query point and searching only through elements stored in buckets containing that point. In addition, since LSH is a hashing-based scheme, it can naturally be extended to dynamic datasets where insertion and deletion operations need to be supported.

More formally, let H be a family of hash functions mapping $\mathbb{R}^d$ to some universe U. For any two points x and y, one can choose a function h from H uniformly at random and analyze the probability that $h(x)=h(y)$. The family H is called "locality sensitive" if it satisfies the following conditions given a distance measure D:

DEFINITION 1. A function family $H=\{h: \mathbb{R}^d \rightarrow U\}$ is called $(R, cR, p_1, p_2)$-sensitive if for any two points $x, y \in \mathbb{R}^d$
if $D(x,y) \leq R$ then $Pr_H[h(x)=h(y)] \geq p_1$
if $D(x,y) \geq cR$ then $Pr_H[h(x)=h(y)] \leq p_2$ For an LSH function family to be useful it has to satisfy the inequalities $c>1$ and $p_1>p_2$. In this case, the LSH family can be used to design an efficient algorithm to solve the R-near neighbor reporting problem:

DEFINITION 2. Given a set of P points in a d-dimensional space $\mathbb{R}^d$ and parameters $R>0$, $\delta>0$, construct a data structure that, given any query point q, reports each R-near neighbor of q in P with probability $1-\delta$.

Typically, one cannot use H directly, since the gap between $p_1$ and $p_2$ may be small. An amplification process is used to achieve a desired probability of collision. This amplification process involves concatenating several functions chosen from H.

The basic LSH indexing methods can be described as follows. For an integer k, we first define the function family $G=\{g: \mathbb{R}^2 \rightarrow U^k\}$ such that $g \in G$ is given by $g(q)=(h_1(q), \ldots, h_k(q))$ where $h_j \in H$ for $1 \leq j \leq k$ (i.e., g is the concatenation of k LSH functions). For an integer T, we then choose $g_1, \ldots, g_T$ from G independently and uniformly at random. Each of these functions $g_i$ for $1 \leq i \leq T$ is used to construct one hash table where all the elements in the dataset are hashed using $g_i$. This data structure, comprising T hash tables in total, is used to find matches to queries. Given a query q, a first step is to generate a candidate set of neighbors by the union of all buckets to which the query q is hashed. False positives are then removed from this candidate set, and objects are ranked according to their distances from the query object q.

Intuitively, concatenating multiple LSH functions to produce each $g_i$ makes the probability of distant objects colliding small. However, it also reduces the collision probability of nearby objects. This results in the need to create and query multiple hash tables constructed with different $g_i$.

Different LSH families can be used for different choices of D. LSH families may be used based on p-stable distributions for $l_p$ norms:

DEFINITION 3. A distribution $\Gamma$ is called p-stable if there exists $p \geq 0$ such that for any n real numbers $v_1, \ldots, v_n$ and i.i.d. variables $X_1, \ldots, X_n$ drawn from $\Gamma$, the random variable $\Sigma_i v_i X_i$ has the same distribution as the variable $(\Sigma_i |v_i|^p)^{1/p} X$ where X is a random variable with distribution $\Gamma$.

A p-stable distribution can be used to generate a hash function that obeys a locality sensitive property. Given a random vector a of dimension d whose each entry is chosen independently from a p-stable distribution, the dot product of two vectors $v_1$ and $v_2$ with a projects these vectors onto the real line. It follows from p-stability that for the vectors, the distance between their projects $(a.v_1 - a.v_2)$ is distributed as $D(v_1, v_2) X$ where X is a p-stable distribution. If the real line is divided into equi-width segments, and vectors are assigned hash values based on which segments they project onto when taking the dot product with a, then it is clear that this hash function will be locality preserving.

More formally, one can define hash functions based on this idea as:

$$h_{a,b}(v) = \lfloor (a.v+b)/W \rfloor \quad (12)$$

where a is a d dimensional vector with entries chosen independently from a p-stable distribution as described above, and b is a real number chosen uniformly from the range [0, W]. Each hash function $h_{a,b}: \mathbb{R}^d \to \mathbb{Z}^+$ maps a vector v onto the set of integers.

For the p=2 case (i.e., the $l_2$ norm corresponding to the Euclidean distance metric), these hash functions can be created using the Gaussian distribution defined as:

$$g(x) = \frac{1}{\sqrt{2\pi}} e^{-x^2/2} \quad (13)$$

which is known to be 2-stable.

For any function $g_i$, the probability that $g_i(x) = g_i(q)$ where x is an R-neighbor of q, is at least $p_1^k$. The probability that $g_i(x) = g_i(q)$ for some $i=1, \ldots, T$ is then at least $1-(1-p_1^k)^T$. If one sets $T = \log_{1-p_1^k} \delta$ so that $(1-p_1^k)^T \leq \delta$, then any R-neighbor of q is returned by the algorithm with probability at least $1-\delta$. While the worst case performance of this approach is linear, the algorithm typically has a sublinear time on many datasets.

To choose k, note that while larger values of k lead to hash functions that are more selective, they also necessitate more hash tables T to reduce false negatives to a desired rate. To address this tradeoff—between hash functions that lead to smaller hash table buckets but more hash tables, and hash functions that lead to larger hash table buckets but fewer hash tables—one may make use of a practical approach that is often recommended to optimize the parameter k. This involves a preliminary training phase using a small number of data points and a set of sample queries. The value of k that provides the best performance is used to develop the LSH data structure.

The basic LSH algorithm described above efficiently discovers matches to a query within a distance R. The amount of work performed by LSH implicitly depends on the choice of R, since larger values of R translate to declaring matches even if data points differ substantially. To detect these matches that differ substantially, and are therefore more likely to hash to different values on any particular function $g_i$, many more tables are needed. This leads to the amount of work performed by LSH increasing with R.

As noted above, the goal of unsupervised anomaly detection based on finding the k-nearest neighbors to a query differs slightly from the basic LSH problem. LSH is optimized to find points within a given radius, and is parameterized by the choice R. In contrast to this, the goal here is to find a specific number of closest matches.

This difference means that for queries that are not anomalies, one can reduce the amount of work done by traditional LSH significantly. These cases can be efficiently resolved by carrying out an initial search with a small value of R. Conversely, for points that are anomalies, one incurs the additional work needed to search a larger distance R for the k nearest neighbors. Since anomalies occur infrequently by definition, the amortized performance of this approach leads to a substantial reduction in time.

The search for matches is therefore carried out by maintaining multiple LSH data structures (each with multiple hash tables) for increasing values of R. As an additional optimization to this process, one may choose expansions to the distance R that are geometrically increasing, i.e., the sequence of distances used to find k-nearest neighbors to a query is $R = r_0, r_0 \epsilon, r_0 \epsilon^2, \ldots, \mathcal{R}$, where $\mathcal{R}$ is an upper bound on the distances of potential k-nearest neighbors. This approach avoids incrementally increasing R in cases where matches are rare and it is likely that a much larger radius is needed to find k-nearest neighbors.

It is believed that an LSH-based variation of the k-NN method such as that described above can provide predictive accuracy similar to the k-NN method while greatly reducing processor runtimes.

Multi-Task Learning Methods Combining Supervised and Unsupervised Learning

As noted above, anomaly detection methods can provide useful estimations of risks associated with rare events, and in some instances may even outperform supervised learning methods. A more precise estimation of risk may be obtained, however, if positive and negative labels are available and used to augment an anomaly detection method. While the absence of a large number of positive examples makes it difficult for supervised learning methods to generalize and provide precise indications of risk for rare events, the information in positive and negative labels may nonetheless be exploited to counter a limitation of unsupervised learning methods. Specifically, unsupervised learning methods may paradoxically consider both the healthiest and the unhealthiest individuals in a population as being high risk if both are identified as anomalies. By making use of both positive and negative label information, the directionality of anomalies may be encoded so that the categorization of risk can focus mainly on anomalies in an unhealthy direction.

A hybrid approach may accomplish this by using a multi-task learning method that combines supervised and unsupervised learning methods. Generally, multi-task learning methods solve two or more problems together. The multi-task learning method disclosed herein treats supervised and unsupervised (e.g., anomaly detection) learning methods as related tasks, and may generate model data by simultaneously solving for parameters according to both supervised and unsupervised learning criteria. This is distinguishable from "semi-supervised learning" methods that augment a certain amount of labeled training data with additional, unlabeled training data.

Figure 4:
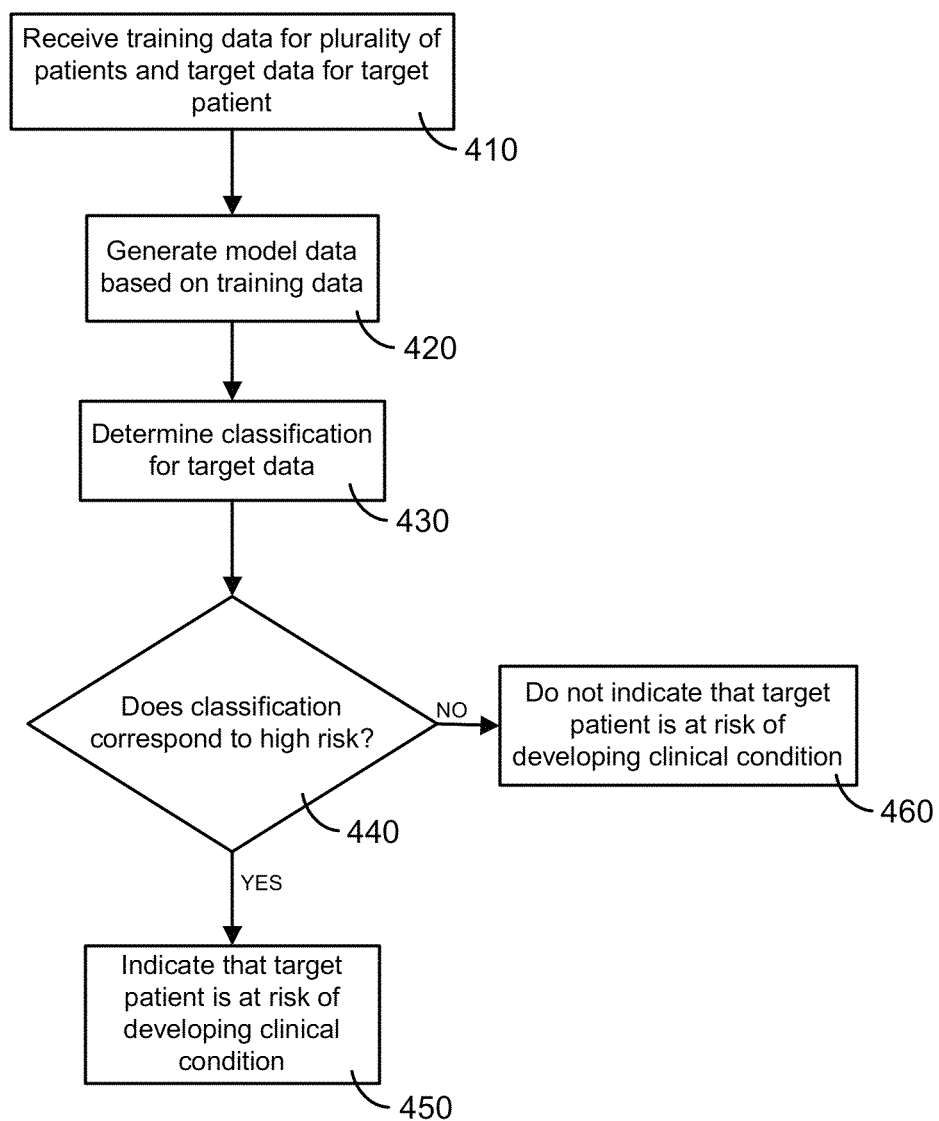
FIG. 4 illustrates an exemplary block diagram of a method for assessing the risk of developing a clinical condition using a multi-task learning method that combines an unsupervised learning method and a supervised learning method.

FIG. 4 illustrates an exemplary block diagram of a method 400 for assessing the risk of developing a clinical condition using a multi-task learning method that combines an unsupervised learning method and a supervised learning method. The clinical condition for which risk is being assessed may be a clinical condition such as death, stroke, sepsis, coma, or wound infection, for example.

The method 400 may receive training data for a plurality of patients and target data for a target patient (block 410). The training data may include label data indicating whether each of the plurality of patients is positively associated with the clinical condition for which the target patient's risk is being assessed. The training data may also include data relating to a variety of factors for each of the patients in the training sample, such as demographics (e.g., gender, age), comorbidity (e.g., presence of a particular disease), laboratory results (e.g., creatinine level, albumin level) and/or procedural factors (e.g., type of surgical procedure performed on a patient, amount of work done by a surgeon on a patient), for example. The target data corresponds to the patient whose risk is being assessed (i.e., the target patient), and may include data relating to some or all of the factors to which the training data relates.

In some embodiments, the method 400 may receive the target data when the training data is received. In other embodiments, the target data may be received at an earlier or later time. In some embodiments, the method 400 may receive either or both of the target data and the training data in a single stream of data. In other embodiments, either or both of the target data and the training data may be received piecemeal over an extended period of time.

The method 400 may generate model data based on the training data (block 420). The model data may be generated according to a multi-task learning method. As noted above, a multi-task learning method combines a supervised learning method (i.e., a method that utilizes label data indicating whether each of the training patients is positively associated with the clinical condition with respect to which risk is being assessed) and an unsupervised learning method (i.e., a method that does not utilize that label data for the training patients). A specific multi-task learning method is employed in the embodiment of the method illustrated in FIG. 5. The generation of model data may involve using the received training data to solve for certain parameters that provide a higher-level representation of the training data.

The method 400 may determine a classification for the target data (block 430). This determination may be made at least in part by performing one or more calculations involving the received target data and the generated model data. A specific example of how this determination may be made is described in connection with the embodiment illustrated in the method of FIG. 5, discussed below.

If the classification for the target data is a classification that corresponds to a high level of risk (block 440), the method 400 may indicate that the target patient is at risk of developing the clinical condition (block 450). In some embodiments, the method 400 may indicate that a target patient is at risk of an adverse outcome by setting the value of a data field representing patient risk. In some embodiments, the method 400 may indicate that a target patient is at risk of an adverse outcome by generating or providing a report. In some embodiments, the method 400 may indicate that a target patient is at risk of an adverse outcome by generating or providing an input to another system or program, such as an acuity adjustment system or program. If the classification for the target data is not a classification that corresponds to a high level of risk (block 440), the method 400 may not indicate that the target patient is at risk of developing the clinical condition (block 460).

Although the method 400 of FIG. 4 depicts a classification that determines in a binary fashion whether a target patient is at high risk of developing the clinical condition (block 430), the method 400 may additionally (or alternatively) calculate a risk score for the target data that is continuous or has more than two discrete values. Like the determination of a classification at block 430, the risk score may be based on one or more calculations involving the target data and the model data. If a risk score is calculated, the method 400 may then additionally (or alternatively) indicate the extent to which the target patient is at risk of developing the clinical condition.

Figure 5:
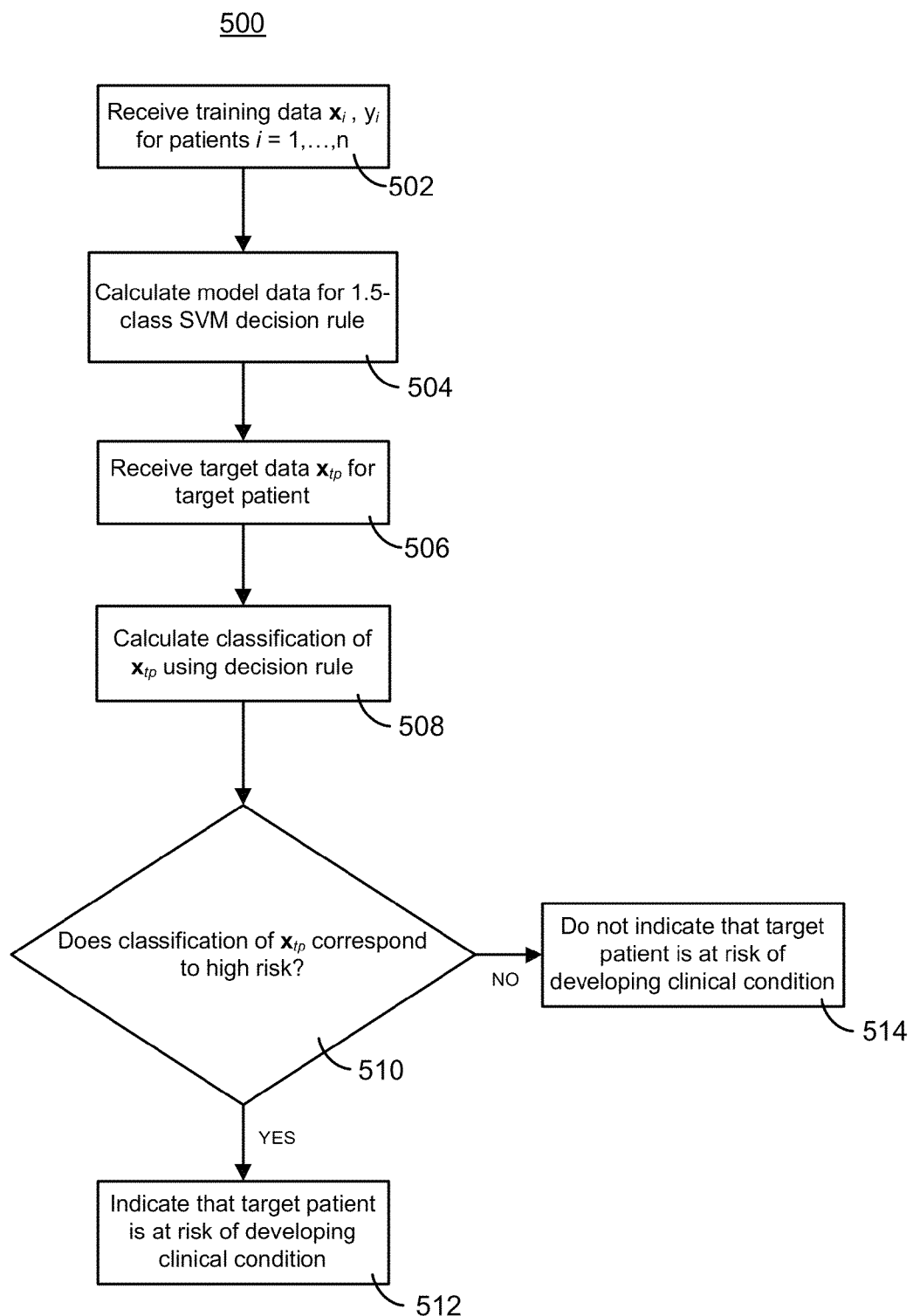
FIG. 5 illustrates an exemplary block diagram of a method for assessing the risk of developing a clinical condition using a 1.5-class SVM method that combines a 1-class SVM method and a 2-class SVM method.

FIG. 5 illustrates an exemplary block diagram of a method 500 for assessing the risk of developing a clinical condition using a hybrid method referred to herein as a "1.5-class SVM" method. The 1.5-class SVM method combines a 1-class SVM method and a 2-class SVM method, by jointly leverages information available through both supervised and unsupervised risk stratification to learn a decision boundary for clinical decision making.

The method 500 may receive training data $x_i$, $y_i$ for patients $i=1,\ldots,n$ (block 502). In some embodiments, each $x_i$ may be a multidimensional vector having one dimension for each feature taken into account (e.g., age, weight, preoperative albumin level, etc.), and $y_i$ may be label data.

Based on the training data $x_i$, $y_i$ the method 500 may calculate model data according to a decision rule for a 1.5-class SVM method that combines a supervised 2-class SVM method and an unsupervised 1-class SVM method (block 504).

Binary or 2-class SVM training focuses on learning a hyperplane in a high-dimensional feature space that can be used for classification. Given a training set $\{(x_i, y_i)|x_1 \in \mathbb{R}^m, y_i \in \{+1, -1\}\}_{i=1}^n$ the soft margin SVM formulation aims to solve the following constrained optimization problem:

$$\min_{w,\xi} \frac{1}{2}\|w\|^2 + C\sum_{i=1}^n \xi_i \quad (14)$$

$$\text{s.t.} \quad y_i(w^T x_i - b) \geq 1 - \xi_i \; \forall \, i = 1, \ldots, n$$

$$\xi_i \geq 0$$

where the constant C reflects the cost of misclassification and the $\xi_i$ correspond to the slack variables of the soft margin SVM. The dual form of the 2-class SVM is given by:

$$\max_\alpha \sum_{i=1}^n \alpha_i - \frac{1}{2}\sum_{i=1}^n \sum_{j=1}^n \alpha_i \alpha_j y_i y_j x_i x_j \quad (15)$$

$$\text{s.t.} \quad 0 \leq \alpha_i \leq C \; \forall \, i = 1, \ldots, n$$

$$\sum_{i=1}^n \alpha_i y_i = 0$$

For problems where the data is not linearly separable, training examples can be projected into a higher dimension feature space using the mapping $\phi(.)$. Because the dual form of the SVM problem only depends on a dot product of the training examples, it can be solved efficiently using a kernel evaluated directly with a nonlinear function in the input space. The decision rule for predicting the label (i.e., classification) of a new example x is then given by $\hat{y} = \text{sgn}(w^T \phi(x) - b)$.

1-class SVM aims to estimate the support S of a high-dimensional distribution such that the probability that a point drawn from the input space lies outside S is low. Roughly speaking, in contrast to the 2-class SVM method, which separates two classes in the feature space by a hyperplane, the 1-class SVM attempts to separate the entire dataset from the origin. The 1-class SVM method is addressed above as an example of an anomaly-detection method, but is revisited here using terms consistent with those in the discussion of 2-class SVM. Given training data of the form $\{(x_i)|x_i \in \mathbb{R}^d\}_{i=1}^n$ (i.e., with the class labels either not available or ignored for training in an unsupervised setting), the 1-class SVM solves the following quadratic problem (which penalizes feature vectors not separated from the origin, while simultaneously trying to maximize the distance of this hyperplane from the origin):

$$\min_{w,\psi,\rho} \frac{1}{2}\|w\|^2 - \rho + C\sum_{i=1}^n \psi_i \quad (16)$$

$$\text{s.t. } w^T\phi(x_i) - \rho \geq (-\psi_i) \; \forall \; i = 1, \ldots, n$$

$$\psi_i \geq 0$$

where the constant C expresses the tradeoff between incorporating outliers that are not separated from the origin and minimizing the support region. The dual form of the 1-class SVM problem is:

$$\min_\alpha \sum_{i=1}^n \sum_{j=1}^n \alpha_i \alpha_j \phi(x_i)\phi(x_j) \quad (17)$$

$$\text{s.t. } 0 \leq \alpha_i \leq C \; \forall \; i = 1, \ldots, n$$

$$\sum_{i=1}^n \alpha_i = 1$$

The decision rule for predicting whether a new example x lies within the region of high probability is then given by $\hat{y} = \text{sgn}(w^T\phi(x) - \rho)$ with $\hat{y} \leq 0$ denoting the detection of an outlier.

As noted above, the 1.5-class SVM method combines the 2-class and 1-class SVM methods. Given the training set $\{(x_i, y_i)|x_i \in \mathbb{R}^d, y_i \in \{+1, -1\}\}_{i=1}^n$, 1.5-class SVM integrates penalties for both the 2-class and 1-class SVM formulations, and minimizes the objective function below while satisfying the constraints associated with both 2-class and 1-class SVM training.

$$\min_{w,\psi,\xi,b,\rho} \frac{1}{2}\|w\|^2 - \rho + C_1\sum_{i=1}^n \psi_i + C_2\sum_{i=1}^n \xi_i \quad (18)$$

$$\text{s.t. } w^T\phi(x_i) - \rho \geq (-\psi_i) \; \forall \; i = 1, \ldots, n$$

$$y_i(w^T\phi(x_i) - b) \geq 1 - \xi_i \; \forall \; i = 1, \ldots, n$$

$$\psi_i \geq 0$$

$$\xi_i \geq 0$$

$C_1$ and $C_2$ in the formulation above denote the costs assigned to penalties for the 1-class and 2-class SVM problems. Since the formulation above represents a summation of quadratic problems, the overall training problem remains quadratic. The dual formulation of the 1.5-class SVM problem is then given below:

$$\max_{\alpha,\gamma} \sum_{i=1}^n \alpha_i - \frac{1}{2}\sum_{i=1}^n \sum_{j=1}^n (\alpha_i y_i + \gamma_i)(\alpha_j y_j + \gamma_j)K(x_i, x_j) \quad (19)$$

$$\text{s.t } 0 \leq \gamma_i \leq C_1 \; \forall \; i = 1, \ldots, n$$

$$0 \leq \alpha_i \leq C_2 \; \forall \; i = 1, \ldots, n$$

$$\sum_{i=1}^n \gamma_i = 1$$

$$\sum_{i=1}^n \alpha_i y_i = 0$$

The approach above presents different choices for a decision boundary associated with the 1.5-class SVM decision rule. In some embodiments, the decision boundary for the decision rule may be set to $w^T\phi(x)-\rho$, which can be interpreted as a modification of the 1-class SVM result. In other embodiments, the decision boundary may be set to $w^T\phi(x)-b$, which can be interpreted as an extension of the 2-class SVM case. In either case, the model data calculated for the 1.5-class SVM decision rule (at block 504) may include the vector w in the formulation of Equation 18.

The method 500 may receive target data $x_{tp}$ for a target patient (block 506). While FIG. 5 depicts this as a step occurring after the steps of receiving the training data $x_i$, $y_i$ and calculating the model data, the target data $x_{tp}$ may in some embodiments be received prior to, between, or contemporaneously with any of those steps.

The method 500 may calculate a classification of the target data $x_{tp}$, using the target data $x_{tp}$ and the calculated model data, according to the 1.5-class SVM decision rule (block 508) In some embodiments, the decision rule may use the decision boundary $w^T\phi(x)-\rho$. In other embodiments, the decision rule may use the decision boundary $w^T\phi(x)-b$.

If the classification corresponds to a high risk of developing the clinical condition (block 510), the method 500 may indicate that the target patient is at risk of developing the clinical condition (block 512). In some embodiments, the method 500 may indicate that a target patient is at risk of an adverse outcome by setting the value of a data field representing patient risk. In some embodiments, the method 500 may indicate that a target patient is at risk of an adverse outcome by generating or providing a report. In some embodiments, the method 500 may indicate that a target patient is at risk of an adverse outcome by generating or providing an input to another system or program, such as an acuity adjustment system or program. If the classification does not correspond to a high risk of developing the clinical condition (block 510), the method 500 may not indicate that the target patient is at risk of developing the clinical condition (block 514).

Although the method 500 of FIG. 5 depicts a classification that determines in a binary fashion whether a target patient is at high risk of developing the clinical condition (block 508), the method 500 may additionally (or alternatively) calculate a risk score for the target data that is continuous or has more than two discrete values. Like the determination of a classification of block 508, the risk score may be based on one or more calculations involving the target data and the model data. For example, the risk score may be, or reflect, the distance between the target data $x_{tp}$ and the decision boundary $w^T\phi(x)-\rho$ or $w^T\phi(x)-b$. If a risk score is calculated, the method 500 may then additionally (or alternatively) indicate the extent to which the target patient is at risk of developing the clinical condition.

Assessing Risk Using Fewer Variables

The costs and burdens associated with predicting adverse outcomes may be lessened by reducing the amount of data that must be collected for building accurate risk stratification models. It has been observed that previous outcomes-analysis studies on NSQIP typically flatten in terms of accuracy with roughly 10 variables. This is primarily because the variables are too rare, internally correlated, or not sufficiently explanatory to contribute meaningfully for risk adjustment or prediction. The ability to translate clinical data into acuity models is relevant not only to outcomes analyses, but also to the goal of predicting patient risk. However, this process depends critically on the presence of validated data that can be used both to train models through inductive inference and to apply these models to individual patients in the future.

With respect to NSQIP, for example, the collection of audited and verified data is both one of its main strengths and one of its major challenges. NSQIP has developed into the leading standard of acuity-based research for surgery. Each hospital participating in NSQIP is required to undergo audit visits and meet stringent guidelines that represent some of the highest in the industry—over 90% for inter-rater reliability (IRR). Data is gathered by nurse data-coordinators and submitted centrally. This verified data is then utilized to construct risk models. NSQIP creates observed-to-expected ratios (O/E) for adverse events for each institution to allow comparison between institutions and to assess progress.

While the kinds of data collected by NSQIP are a valuable resource to develop acuity models with high predictive accuracy, and can be generalized to the set of variables that can potentially be used as a basis for patient care, they are resource-intensive to maintain. These data generally require nursing abstractors and custom information technology links to assist with abstracting data for verification from administrative sources that are different at each institution. The data can be categorized by source and type. Each category of data requires a different interface and method for collection, with variable impact on nursing or registrar abstractor time. The NSQIP sampling methodology utilizes laboratory data, which at most institutions are gathered manually and entered into the computerized system. Some institutions have developed direct interfaces at great expense. In NSQIP acuity-adjusted data over the years 2005-2008, only serum albumin was utilized consistently as a continuous variable in the acuity adjustment models. Other laboratory results appear as categorized variables intermittently (for example, creatinine>1.2, or serum glutamic oxaloacetic transaminase [SGOT]>40). In the setting of scarce resources with intense demands for efficiency, it is often not worthwhile to collect all categories of data. Understanding the value of each category may lead to improved efficiency while preserving accuracy. It should be noted that the issue of collecting data is relevant both for forming the initial models (where a large number of variables need to be collected from many patients) and the subsequent application of these models to patients. In this context, the demands of data collection are both resource-intensive and persistent.

These burdens may be eased by utilizing a greatly reduced number of NSQIP variables for health risk assessments. An example of this may be seen by focusing on NSQIP data relating to death and morbidity outcomes within 30 days following surgery, and 86 NSQIP variables collected before the start of surgery that have a correlation to 30-day death or morbidity. A list of these variables is as follows: Gender, CPT Code, Work Relative Value Unit, Inpatient/outpatient, Transfer status, Age of patient, Year of Hospital Admission, Year of admission to the hospital, Year of Admission to Surgery, Year of Operation, Year the surgical procedure is performed, Principal anesthesia technique, Level of Residency Supervision, Surgical Specialty, Height, Weight, Diabetes mellitus with oral agents or insulin, Current smoker within one year, Pack-years of smoking, EtOH>2 drinks/day in 2 wks before admission, Dyspnea, Do not resuscitate (DNR) status, Functional health status Prior to Current Illness, Functional health status Prior to Surgery, Ventilator dependent, History of severe COPD, Current pneumonia, Ascites, Esophageal varices, Congestive heart failure (CHF) in 30 days before surgery, History of myocardial infarction 6 mos prior to surgery, Previous percutaneous coronary intervention (PCI), Previous cardiac surgery, History of angina in 1 month before surgery, Hypertension requiring medication, History of revascularization/amputation for periph. vascular disease, Rest pain/gangrene, Acute renal failure, Currently on dialysis (pre-op), Impaired sensorium, Coma >24 hours, Hemiplegia, History of transient ischemic attacks (TIA), CVA/Stroke with neurological deficit, CVA/Stroke with no neurological deficit, Tumor involving CNS, Paraplegia, Quadriplegia, Disseminated cancer, Open wound/wound infection, Steroid use for chronic condition, >10% loss body weight in last 6 months, Bleeding disorders, Transfusion >4 units PRBCs in 72 hours before surgery, Chemotherapy for malignancy in <=30 days pre-op, Radiotherapy for malignancy in last 90 days, Preoperative Systemic Sepsis, Pregnancy, Prior Operation within 30 days, Days from Na Preoperative Labs to Operation, Days from BUN Preoperative Labs to Operation, Days from Creatinine Preoperative Labs to Operation, Days from Albumin Preoperative Labs to Operation, Days from Bilirubin Preoperative Labs to Operation, Days from SGOT Preoperative Labs to Operation, Days from ALKPHOS Preoperative Labs to Operation, Days from WBC Preoperative Labs to Operation, Days from HCT Preoperative Labs to Operation, Days from PlateCount Preoperative Labs to Operation, Days from P17 Preoperative Labs to Operation, Days from PT Preoperative Labs to Operation, Days from INR Preoperative Labs to Operation, Pre-operative serum sodium, Pre-operative BUN, Pre-operative serum creatinine, Pre-operative serum albumin, Pre-operative total bilirubin, Pre-operative SGOT, Pre-operative alkaline phosphatase, Pre-operative WBC, Pre-operative hematocrit, Pre-operative platelet count, Pre-operative PTT, Pre-operative International Normalized Ratio (INR) of PT values, Pre-operative PT, Emergency case and Mallampati scale.

A predictor that uses a relatively small subset of the 86 variables provides predictive accuracy similar to that of a predictor using all 86 variables, in some embodiments. Using forward selection based on the Wald statistic to select variables, for example, a predictor based on only 10 or even 5 variables can provide predictive accuracy nearly as good as (e.g., having a statistically insignificant difference than) predictor based on all 86 variables.

The first 10 variables found using this approach for mortality were (in order of predictive value, from highest to lowest based on Wald statistic): functional health status prior to surgery, American Society of Anesthesiologists (ASA) classification, preoperative serum albumin, age, presence of disseminated cancer, preoperative blood urea nitrogen (BUN), do-not-resuscitate (DNR) status, emergent vs. non-emergent case, work relative value unit, and presence of ascites. In some embodiments, only these ten variables are used to predict risk of an adverse outcome for a patient with respect to mortality. In some embodiments, only five of these variables (or, in some embodiments, only the first five variables as listed above) are used to predict risk of an adverse outcome for a patient with respect to mortality. Other embodiments relating to the number and kind of variables are discussed below in connection with FIG. 6.

The first 10 variables for morbidity were (in order of predictive value, from highest to lowest based on Wald statistic): ASA classification, work relative value unit, preoperative serum albumin, emergent vs. non-emergent case, functional health status prior to surgery, inpatient vs. outpatient case, preoperative systemic sepsis, age, steroid use for chronic condition, and weight. In some embodiments, only these ten variables are used to predict risk of an adverse outcome for a patient with respect to a morbidity condition (e.g., one or more diseases, disabilities, etc.). In some embodiments, only five of these variables (or, in some embodiments, only the first five variables as listed above) are used to predict risk of an adverse outcome for a patient with respect to morbidity. Other embodiments relating to the number and kind of variables are discussed below in connection with FIG. 6.

Moreover, a predictor based on only non-laboratory data from the 86 NSQIP variables mentioned above can assess risk nearly as well as a predictor based on all 86 variables. In some embodiments, the patient-related variables used to predict risk exclude all laboratory result data (e.g., preoperative albumin or BUN levels, etc.). Further, a predictor based on only variables collected in an earlier year may assess risk nearly as well as a predictor based on variables collected in a more recent year. In some embodiments, the patient-related variables used to predict risk exclude all data collected within a particular time period (e.g., one year) immediately preceding the time at which risk is predicted, and/or immediately preceding the time(s) that data is collected for a target patient whose risk is being assessed. For example, a risk assessment performed in the year 2011 may exclude all data in the NSQIP database for the year 2011, for the years 2010-11, the years 2009-11, etc.

Predictive accuracy can be compared using a metric known as the "area under the receiver operating curve" (AUROC), with a greater AUROC indicating greater predictive accuracy. A P-Value generally provides a statistical measure of how likely it is that the measured AUROC is purely incidental, rather than an accurate measure of predictive ability. While AUROC is primarily discussed below, those of ordinary skill in the art appreciate that many alternatives are available, including for example, sensitivity, specificity, false positive rate, false negative rate, positive predictive value, negative predictive value, net reclassification improvement and integrated discrimination improvement. Table 1 below presents AUROC and P-Value results for predictive models constructed on the 2007 NSQIP Participant Use File (PUF) using the first 1, 5, or 10 variables listed above (i.e., the first listed variable, the first 5 listed variables, or all 10 listed variables) for mortality and morbidity, respectively, as compared to the predictive model using all 86 NSQIP variables:

TABLE 1

Comparison of AUROC for models constructed with 1, 5 and 10 variables with models constructed using all 86 variables.

| Model | Mortality AUROC | P-Value | Morbidity AUROC | P-Value |
|---|---|---|---|---|
| All Variables | 0.907 | Ref | 0.767 | Ref |
| 10 Variables | 0.902 | 0.889 | 0.759 | 0.524 |
| 5 Variable | 0.889 | 0.642 | 0.750 | 0.184 |
| 1 Variable | 0.689 | <0.001 | 0.654 | <0.001 |

As shown in Table 1, only a small, statistically insignificant decrease in AUROC occurs when going from 86 variables down to 10 or 5 variables, for both mortality and morbidity. Thus, far fewer patient-related variables may be used to accurately predict risk than previously thought.

Table 2 below presents mortality and morbidity AUROC and P-Value results for predictive models constructed on the 2007 NSQIP PUF using all variables, as compared to predictive models constructed on the same patient population without using laboratory results:

TABLE 2

Comparison of AUROC for models constructed without laboratory results with models constructed using all 86 variables.

| Model | Mortality AUROC | P-Value | Morbidity AUROC | P-Value |
|---|---|---|---|---|
| All Variables | 0.907 | Ref | 0.767 | Ref |
| No Laboratory Variables | 0.896 | 0.769 | 0.761 | 0.636 |

As shown in Table 2, only a small, statistically insignificant decrease in AUROC occurs when excluding variables corresponding to laboratory results, for both mortality and morbidity. Thus, despite the fact that certain variables corresponding to laboratory data may be highly correlated to mortality or morbidity outcomes, predictive models that are not based on any laboratory data can compare favorably with predictive models that are based in part on laboratory data.

Table 3 below presents mortality and morbidity AUROC and P-Value results for predictive models constructed on the 2007 NSQIP PUF using all variables, as compared to predictive models constructed on the 2006 NSQIP PUF using all variables:

TABLE 3

Comparison of AUROC for models constructed using 2007 NSQIP PUF with models constructed using 2006 NSQIP PUF.

| Model | Mortality AUROC | P-Value | Morbidity AUROC | P-Value |
|---|---|---|---|---|
| All Variables (2007) | 0.907 | Ref | 0.767 | Ref |
| All Variables (2006) | 0.895 | 0.759 | 0.763 | 0.780 |

The results in Table 3 were determined by evaluating patient outcomes in the 2008 NSQIP PUF (i.e., one or two years later as compared to the 2007 or 2006 NSQIP PUF, respectively). As shown in Table 3, only a small, statistically insignificant decrease in AUROC occurs when using data approximately two years old and excluding data collected within the previous calendar year, for both mortality and morbidity. Thus, despite the fact that more recent data may be expected to be more highly correlated to mortality or morbidity outcomes, predictive models based on older data can compare favorably with predictive models based on the recent data.

Accordingly, related categories of data may only incrementally increase the accuracy of existing risk stratification models. A long-held dictum of the management community has been to seek efficiencies through the 80:20 rule or Pareto principle. For example, it is typical that 80% of the commissions at a brokerage are generated by 20% of the brokers. This principle may be true in health care settings as well, where 80% of the risk related to the patient may be modeled using 20% of the data, or possibly 20% of the effort to gather the data. In this sense the incremental benefit of each new variable or new category of variables, each with its own gathering and verification system, can be viewed critically.

Thus, significant degradation of the accuracy of predictive models may be avoided by changing the number of variables, the categories of variables, and the times at which these variables were collected. Models to predict adverse surgical outcomes may be constructed using fewer variables, with reduced dependence on laboratory results—and potentially using data that is not recorded in the period immediately preceding model training—while still achieving accuracy similar to a more data-intensive approach.

This result motivates the creation of acuity models that can be constructed and applied in an affordable and time-efficient manner with low complexity. For example, laboratory results such as albumin levels have been consistently important in the NSQIP dataset while creating models of patient risk. Yet to obtain this one laboratory value at the typical institution would require either a laboratory interface or a separate method for clinical lookup. While albumin has been proven to be valuable in risk stratification, it may be possible to construct predictive models without it that have similar accuracy yet eliminate a level of complexity in the pursuit of quality data that is easier to obtain. In particular, patient demographics and clinical characteristics, which can easily be obtained from patient histories and physical exams, contain a wealth of information that can be exploited to reduce dependence on variables that are more invasive and expensive to measure.

Health care institutions, regulatory and reporting agencies, payers, and even patients increasingly require transparency and reliable outcomes data (preferably with acuity adjustment) in a validated manner. Health care expenditure is rising rapidly and quality projects struggle to justify expenditure in data gathering and capture. Each variable and additional type or category of variable comes at a greater expense stressing ever-tightening budgets and resources. Methods to improve efficiency without sacrificing accuracy are essential to the continued growth of the quality and outcomes movement in health care.

The NSQIP example above may be extended more broadly to other datasets and clinical disciplines. Moreover, addressing the challenges of collecting data for risk stratification (i.e., time and financial costs, or need for invasive tests to measure some parameters) may have further relevance in addressing the burden of cognitive overload. Reducing the number of variables needed to predict patient risk creates the opportunity to identify core data elements that can be compactly presented to caregivers for decision-making.

Figure 6:
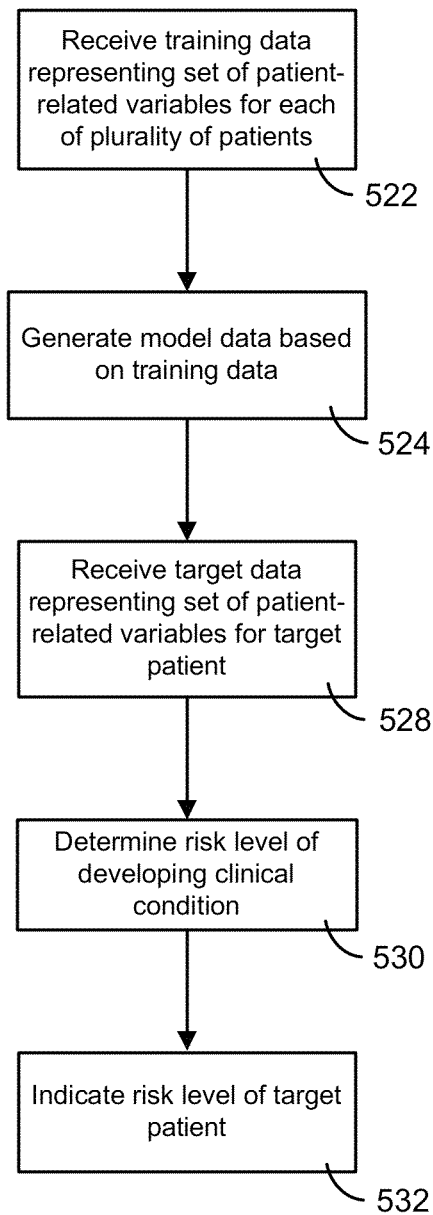
FIG. 6 illustrates an exemplary block diagram of a method for assessing the risk of developing a clinical condition using a limited set of patient-related variables.

FIG. 6 illustrates an exemplary block diagram of a method 520 for assessing the risk of developing a clinical condition using a limited set of patient-related variables. The method 520 may receive training data representing a set of patient-related variables for each of a plurality of patients (block 522). In some embodiments, the training data is received from a database such as the NSW database. However, the training data could alternatively be obtained from other databases, which could include any of a variety of datasets, any registry, a corporate data store, a research data set, a surgical log, etc. The training data may be labeled or unlabeled training data, or a combination of both, according to the embodiment.

In some embodiments, where the clinical condition is a mortality condition (i.e., death), the set of patient-related variables includes some or all of: functional health status prior to surgery, ASA classification, preoperative serum albumin, age, presence of disseminated cancer, preoperative BUN, DNR status, emergent vs. non-emergent case, work relative value unit, and presence of ascites. In some of these embodiments, the set of patient-related variables consists of between three and ten, between four and ten, between five and ten, or all ten of these ten variables. In other of these embodiments, the set of patient-related variables consists of twenty or fewer, fifteen or fewer, or twelve or fewer patient-related variables, where the variables include at least three, at least four, at least five, or all ten of the ten variables listed above.

In some embodiments where the clinical condition is a mortality condition, the set of patient-related variables includes some or all of: functional health status prior to surgery, ASA classification, preoperative serum albumin, age, and presence of disseminated cancer. In some of these embodiments, the set of patient-related variables consists of between three and five, between four and five, or all five of these five variables. In other of these embodiments, the set of patient-related variables consists of twenty or fewer, fifteen or fewer, twelve or fewer, or ten or fewer patient-related variables, where the variables include at least three, at least four, or all five of the five variables listed above.

In some embodiments, where the clinical condition is a morbidity condition (e.g., one or multiple diseases, disabilities, etc.), the set of patient-related variables includes: ASA classification, work relative value unit, preoperative serum albumin, emergent vs. non-emergent case, functional health status prior to surgery, inpatient vs. outpatient case, preoperative systemic sepsis, age, steroid use for chronic condition, and weight. In some of these embodiments, the set of patient-related variables consists of between three and ten, between four and ten, between five and ten, or all ten of these ten variables. In other of these embodiments, the set of patient-related variables consists of twenty or fewer, fifteen or fewer, or twelve or fewer patient-related variables, where the variables include at least three, at least four, at least five, or all ten of the ten variables listed above.

In some embodiments where the clinical condition is a morbidity condition, the set of patient-related variables includes: ASA classification, work relative value unit, preoperative serum albumin, emergent vs. non-emergent case, and functional health status prior to surgery. In some of these embodiments, the set of patient-related variables consists of between three and five, between four and five, or all five of these five variables. In other of these embodiments, the set of patient-related variables consists of twenty or fewer, fifteen or fewer, twelve or fewer, or ten or fewer patient-related variables, where the variables include at least three, at least four, or all five of the five variables listed above.

In some embodiments, the set of patient-related variables excludes all variables corresponding to laboratory results. For example, the set of patient-related variables may exclude variables such as preoperative serum albumin, preoperative BUN, creatinine, and SGOT. In some embodiments, the set of patient-related variables may additionally or alternatively exclude all training data collected within a particular period of time (e.g., within the previous one year, or within the current and previous calendar year) immediately prior to receiving the training data at block 522. In some embodiments, all data collected within the year (or calendar year) that the training data is received at block 522, and/or within the preceding year (or calendar year), may be excluded.

The method 520 may generate model data based on the received training data (block 524). The model data may correspond to any traditional risk assessment technique, or to any of the risk assessment techniques discussed above (e.g., MEB, k-NN, 1-class SVM, 1.5-class SVM, etc.).

The method 520 may receive target data representing the set of patient-related variables for a target patient (block 528). While FIG. 6 depicts this as occurring after receiving the training data and generating the model data, the target data may in some embodiments be received prior to, between, or contemporaneously with any of those actions, and may or may not be a part of the training data used to generate the model data. The set of patient-related variables for the target patient includes the same variable types (e.g., age, functional health status prior to surgery, etc.) as the set of patient-related variables represented by the training data for the plurality of patients, in an embodiment, but with values specifically corresponding to the target patient.

The method 520 may determine a risk level for the target patient of developing the clinical condition (block 530). Determining the risk level includes performing one or more calculations involving the received target data and the generated model data, in an embodiment. The calculations correspond to the risk assessment technique that is utilized when generating the model data at block 524 (e.g., MEB, k-NN, 1-class SVM, 1.5-class SVM, etc.), as discussed above. As permitted according to the utilized risk assessment technique, determining the risk level may include making a binary determination (e.g., classifying a risk level as one of two classes), a determination with more than two levels (e.g., classifying a risk level as one of three or more classes), or a determination of a value that is continuous or has many values (e.g., determining a risk score).

The method 520 may indicate the target patient's risk level of developing the clinical condition (block 532). In some embodiments, the method 520 may indicate the risk level by setting the value of a data field representing patient risk. In some embodiments, the method 520 may indicate the risk level by generating or providing a report. In some embodiments, the method 520 may indicate the risk level by generating or providing an input to another system or program, such as an acuity adjustment system or program. The indication may reflect a binary, continuous, or other determination made at block 530, according to the embodiment. Another example of an acuity adjustor that could be used effectively in such models is Charlson Scoring.

While the method 520 only shows receiving training data and target data representing the same set of patient-related variables (blocks 522, 228, respectively), other training and/or target data representing other patient-related variables may also be received. In an embodiment, however, the generation of the model data (block 524) and the determination of the risk level (at block 530) are based only on the training and/or target data corresponding to the set of patient-related variables as discussed according to various embodiments above.

Assessing Risk for Surgical Procedures

The National Surgical Quality Improvement Program (NSQIP) was developed to provide risk-adjusted data to hospitals for 30-day mortality and morbidity. Risk adjustment in NSQIP attempts to capture information related to both patient factors, including co-morbidities, demographics, and laboratory results, as well as information related to procedural factors, such as the type of operation performed as determined by its current procedural terminology (CPT) code and the amount of work done by the surgeon during the entire episode of care as determined by relative value units (RVU). However, despite this focus on supplementing information related to patients with information related to procedures, there is an absence of variables in NSQIP to robustly quantify operation complexity. The RVU is used to fill this gap by approximating case complexity, but the RVU is a component of fee schedule and does not directly take into account the amount of risk that an individual operation poses. In addition, it abstracts away from the underlying procedure and does not provide enough specificity for the operation performed. It is not, therefore, surprising that the odds ratios of 30-day mortality and morbidity in NSQIP based on RVU are generally close to one.

Conversely, CPT codes retain information about the specific operations performed, but do not directly measure risk. Moreover, these codes span a wide range and need to be categorized before they can be used in logistic regression models for risk adjustment. If the categories are too narrowly defined, the large number of total CPT groups and the resulting small number of cases within each group make these data less useful for risk adjustment. Similarly, if the CPT codes are aggregated into broad categories of anatomic ranges as is current practice, this can greatly limit the granularity at which operational complexity, and consequently the risk associated with specific procedures, can be assessed. For example, CPT codes between 40,000 and 49,999 generally correspond to gastrointestinal operations. Within this range are included both relatively minor operations, such as inguinal hernia repair, as well as very complex procedures, such as pancreaticoduodenectomy. Some solutions have recently attempted to ameliorate some of this problem by analyzing risk adjustment models based on 135 more fine-grained CPT groups than traditionally used. This has become the analytical standard for NSQIP.

In an embodiment, 2-class SVM training may be used to construct models of the relationship between CPT codes and 30-day outcomes. The process of 2-class SVM training is described in more detail above in connection with multi-task learning. 2-class SVM training is formulated as the goal of learning a maximum-margin hyperplane that uses information in features (e.g., CPT codes) to separate observations belonging to two different labeled classes (e.g., patients who experienced adverse outcomes and those that remained event free). The maximum-margin hyperplane corresponds to the decision boundary with the maximal distance from any of the training examples. The choice of a maximum-margin hyperplane is supported by theoretical results in statistical learning that this approach can maximize the ability to predict the correct classification of previously unseen examples. Despite the existence of other algorithmic techniques for modeling, one of the key reasons to use SVMs to learn the relationship between CPT codes and outcomes is due to this property of SVMs to learn optimal separating boundaries. Previous attempts to increase the "granularity" of NSQIP data have centered on grouping like operations into CPT categories, which have ranged from 128 to 135 groups. Using each individual CPT code, as is done here, provides the "floor" for granularity of procedure-related codes. That is to say, each CPT code can be considered as having its own group.

For many real-world datasets, a linear separation that perfectly discriminates between labeled training examples is not possible. SVM training addresses these cases where the data are not linearly separable through different extensions, including the addition of an error term and the re-mapping of the data into a space where the data are linearly separable. The use of re-mapping is particularly effective, and is achieved by projecting the data to a higher dimensional feature space where a linear separation with a maximum-margin hyperplane is possible. This projection is typically achieved by using a kernel function that defines the distance between features in a higher dimensional space. While the maximum-margin hyperplane is linear in the higher dimensional space, the decision contours can be mapped back to a non-linear maximum-margin boundary in the original lower dimensional space.

The ability of SVM training to efficiently solve for maximum-margin hyperplanes using projections into higher dimensions offers further advantages over other learning algorithms. In particular, the ability to learn a model from features that are not linearly separable (i.e., where increasing or decreasing feature values do not consistently correspond to the increased likelihood of a label) is particularly important for the application of learning the relationship between CPT codes and outcomes. Unlike logistic regression, for example, which assumes monotonically increasing or decreasing risk with continuous features and therefore requires CPT codes to be studied as categorical variables, SVM training with projections can handle CPT codes without need for categorization by finding a linear maximum-margin boundary in a higher dimensional space that can provide a non-linear separation of lower dimensional CPT data.

The SVM training process described so far focuses on learning a model that makes binary predictions (e.g., uses CPT codes to make "hard" predictions about whether patients will experience 30-day outcomes or remain event-free depending on which side of the decision boundary they lie on). One of skill in the art can extend this training process to perform SVM regression, i.e., to make "soft" predictions of risk along a continuum. Moreover, while the above embodiments include SVM training, any non-parametric learning technique that maps codes to a linear space may be used.

In some embodiments, the above techniques are applied to codes other than CPT codes (e.g., other medical codes). For example, the above techniques may be applied instead to a set of diagnostic codes (e.g., International Classification of Diseases (ICD) codes, such as ICD-9 codes), or jointly applied to both a set of CPT codes and a set of diagnostic (e.g., ICD) codes. More generally, the above techniques may be applied to any set of codes that exhibits some locality properties and non-linearity properties in relation to a likelihood of an adverse outcome. A set of codes has locality and non-linearity properties if (1) at least some of the codes are grouped in a manner having some correlation to risk level, and (2) at least some of the codes are not arranged linearly with respect to risk level (e.g., not all of the code values increase or decrease as risk level increases or decreases, respectively, and vice versa).

Figure 7:
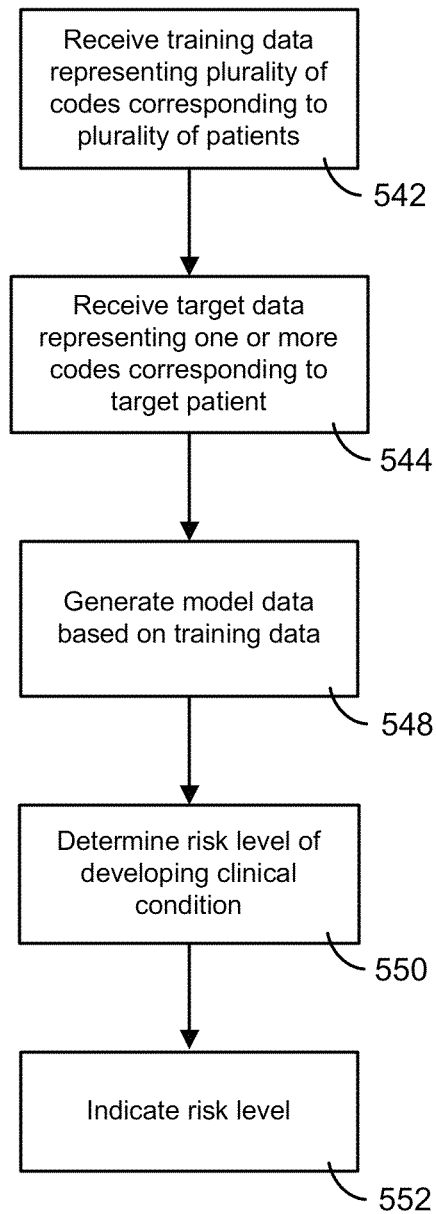
FIG. 7 illustrates an exemplary block diagram of a method for assessing the risk of developing a clinical condition based on codes.

FIG. 7 illustrates an exemplary block diagram of a method 540 for assessing the risk of developing a clinical condition using codes. The method 540 may receive training data representing a plurality of codes corresponding to a plurality of patients (block 542). In some embodiments, each of the codes corresponding to the plurality of patients is a code that belongs to a set of codes having locality and non-linearity properties with respect to a likelihood of developing the clinical condition. In some embodiments, at least some of the codes belong to a set of surgical procedure codes (e.g., CPT codes) and/or at least some of the codes belong to a set of diagnostic codes (e.g., ICD codes). In some embodiments, the training data is received from a database such as the NSQIP database. The training data may be labeled or unlabeled training data, or a combination of both, according to the embodiment.

The method 540 may receive target data representing one or more codes corresponding to a target patient (block 544). While FIG. 7 depicts this as a step occurring after the step of receiving the training data, the target data may in some embodiments be received prior to or contemporaneously with receiving the training data. In some embodiments, each of the one or more codes corresponding to the target patient is a code that belongs to a set of codes having locality and non-linearity properties with respect to a likelihood of developing the clinical condition. In some embodiments, at least one code belongs to a set of surgical procedure codes (e.g., CPT codes) and/or at least one code belongs to a set of diagnostic codes (e.g., ICD codes). In some embodiments, at least one code (e.g., a CPT code) reflects a procedure that may be performed on the target patient in the future. In other embodiments, at least one code (e.g., a CPT code) reflects a procedure that was already performed on the target patient. In some embodiments, each code represented by the target data belongs to the same category as at least one of the codes represented by the training data.

The method 540 may generate model data based on the received training data (block 548). In an embodiment, the model data is generated at least in part by utilizing a non-parametric learning method that maps the codes corresponding to the plurality of patients to a linear space. For example, generating the model data may include utilizing a 2-class SVM learning method.

The method 540 may determine a risk level, corresponding to the target data, of developing the clinical condition (block 550). In an embodiment, determining the risk level includes performing one or more calculations comparing, in the linear space, the one or more codes corresponding to the target patient to the plurality of codes corresponding to the plurality of patients. In some embodiments, determining the risk level includes determining a risk classification for the target data. In some embodiments, determining the risk level additionally or alternatively includes determining a risk score (e.g., a continuous risk score) for the target data.

The method 540 may indicate the risk level, corresponding to the target data, of developing the clinical condition (block 552). In some embodiments, the method 540 may indicate the risk level by setting the value of a data field representing patient risk. In some embodiments, the method 540 may indicate the risk level by generating or providing a report. In some embodiments, the method 540 may indicate the risk level by generating or providing an input to another system or program, such as an acuity adjustment system or program. In some embodiments where a risk classification is determined at block 550, the method 540 indicates whether the target patient is at risk of developing the clinical condition, with the indication being based at least in part on the risk classification. In some embodiments where a risk score is determined at block 550, the method 540 indicates the extent to which the target patient is at risk of developing the clinical condition, with the indication being based at least in part on the risk score. In some embodiments where both a risk classification and a risk score are determined at block 550, the method 540 indicates whether, and the extent to which, the target patient is at risk of developing the clinical condition, with the indication being based at least in part on both the risk classification and the risk score.

Exemplary Data Sources and Outputs

Figure 8:
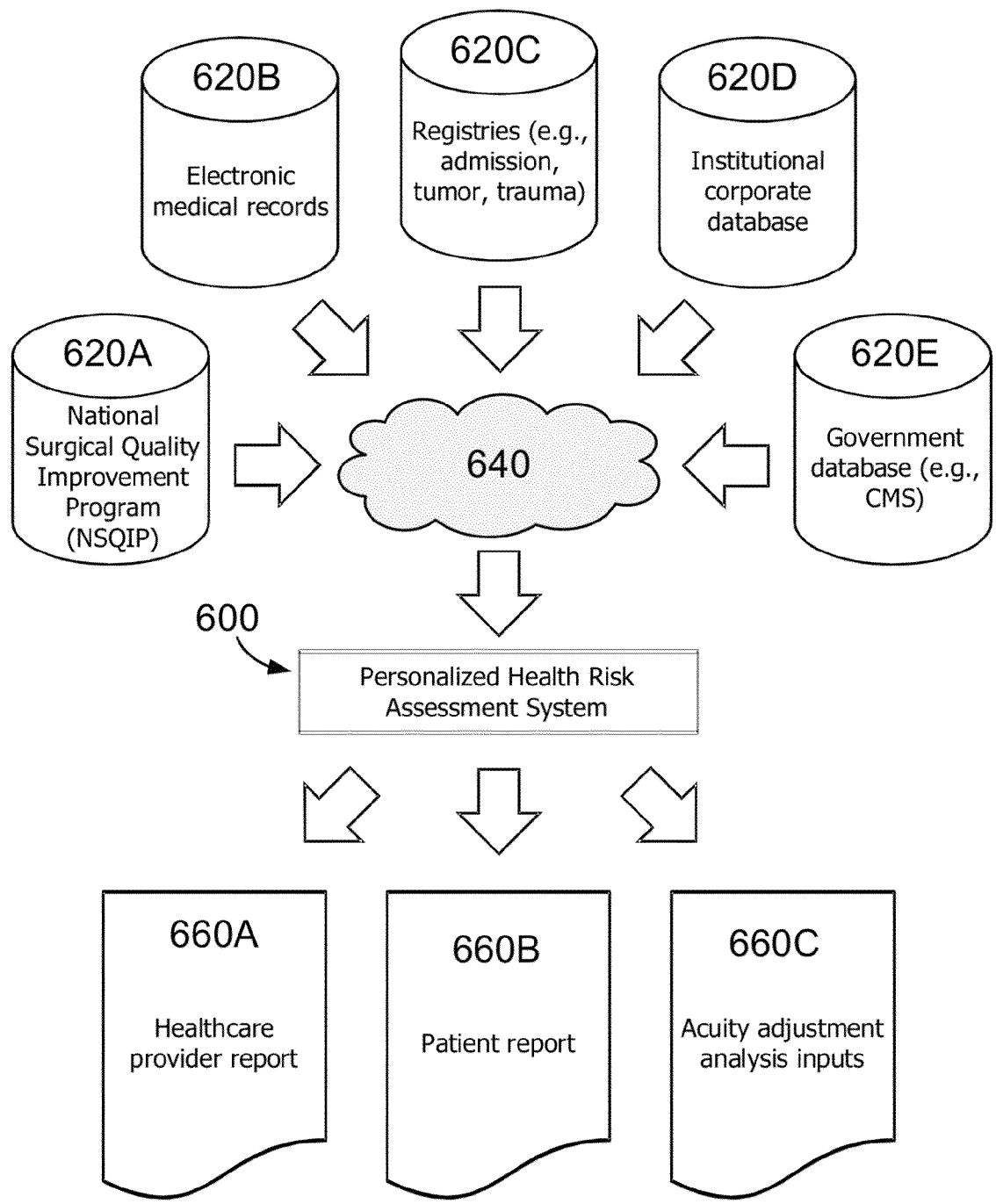
FIG. 8 illustrates an exemplary block diagram of a personalized health risk assessment system including exemplary data sources and outputs.

FIG. 8 illustrates an exemplary block diagram of a personalized health risk assessment system 600 including exemplary data sources 620 and outputs 660. The system 600 may be communicatively linked to a plurality of data sources 620. The data sources 620 may include both training data corresponding to a relatively large number of patients and target data corresponding to a target patient whose health risk is to be assessed. For example, training data may include data from the National Surgical Quality Improvement Program (NSQIP) 620A. Other exemplary data sources, including sources for training data and/or data relating to the target patient, can include electronic medical records 620B, registries 620C (e.g., a tumor, trauma or admission registry), an institutional corporate database 620D associated with health care institutions, and/or a government database 620E (e.g., a database maintained by the Centers for Medicare & Medicaid Services). While FIG. 6 depicts data sources 620A through 620E, the system 600 may extract data from any number of data sources 620 that include training or target patient information that may be used to assess risk.

With respect to the embodiments described above, the training data may be received from a database or registry such as NSQIP national database 620A, electronic medical records 620B, admission, tumor and trauma registries 620C, institutional corporate database 620D, and/or government database 620E. The target data may be received from a database or registry such as electronic medical records 620B and/or admission, tumor or trauma registries 620C, for example.

Each data source may correspond to a database that may be stored at a single location on a single machine or distributed across multiple locations on multiple machines. The system 600 may extract data from the data sources 620 through a communication network 640 (e.g., the Internet, or a combination of external and internal networks), as further described in relation to FIGS. 9 and 10, below.

FIG. 8 also depicts several potential outputs 660 from the personalized health risk assessment system 600. The outputs 660 may include, for example, a report 660A made available to a healthcare provider. The healthcare provider may decide to modify treatment and/or monitoring of the target patient based on the report 660A, for example. The outputs 660 may also include a report 660B made available to the target patient, for example. The report 660B may be used to ensure that a patient is able to provide informed consent to a surgical procedure, for example. As yet another example, the outputs 660 may include inputs 660C to an acuity adjustment analysis. An acuity adjustment analysis compares the risk of an adverse outcome estimated by the health risk assessment system 600 to the actual, observed outcome. Acuity adjustment analyses can provide a useful indicator of performance. For example, management at a healthcare provider may desire to compare the estimated risk for a patient with the actual outcome for the patient in order to help evaluate the person or team charged with providing care to that patient. While FIG. 8 depicts outputs 660A through 660C, the system 600 may provide any number of outputs 660 for any number of different applications.

Indicating target patient risk, as described above in the health risk assessment embodiments, may include generating or providing one or more outputs such as the outputs 660, for example. For example, indicating target patient risk may include generating or providing a report such as the report 660A to a healthcare provider and/or the report 660B to a patient (such as the target patient), and/or generating or providing inputs such as the inputs 660C to an acuity adjustment analysis.

Assessing Risk by Combining Datasets

Multi-institutional databases such as NSQIP generally provide excellent global risk assessment. However, the interaction between these global risk assessments and risk assessments at individual institutions, which may vary in how care is delivered, has been unclear. Integrating risk assessment models from a multi-institution, national source and an institution-specific source can take advantage of both the larger population provided by NSQIP and the more representative population provided by the institution-specific source. As a result, integrated models can provide results superior to models developed using either data source alone. The institution-specific source is more "representative" in the sense that it typically corresponds to a patient population that is more like the target patient (assuming, of course, that the target patient is a patient at that particular institution).

Exemplary Health Risk Assessment System

Figure 9:
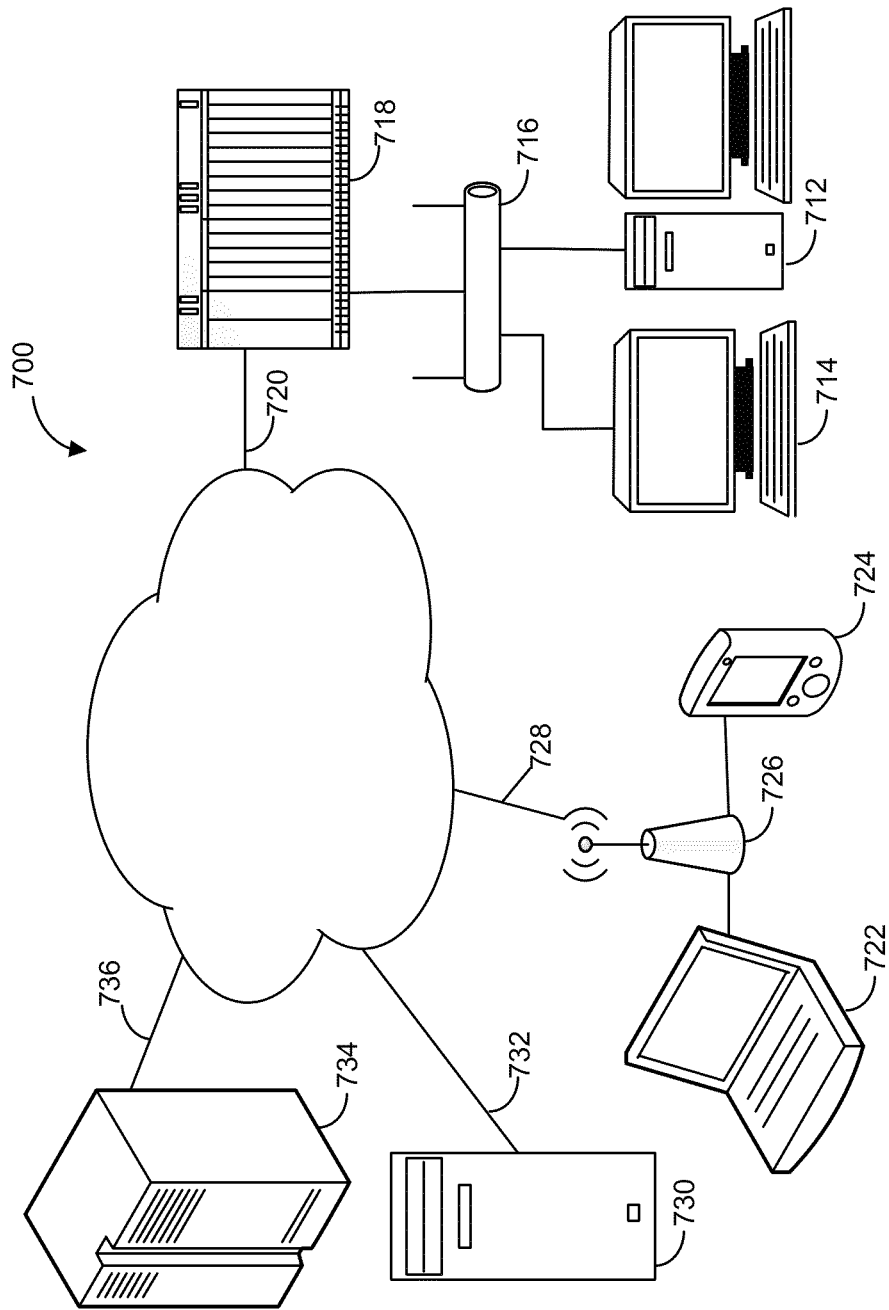
FIG. 9 illustrates an exemplary block diagram of a network and computer hardware that may be utilized in an exemplary personalized health risk assessment system in accordance with the described embodiments.
Figure 10:
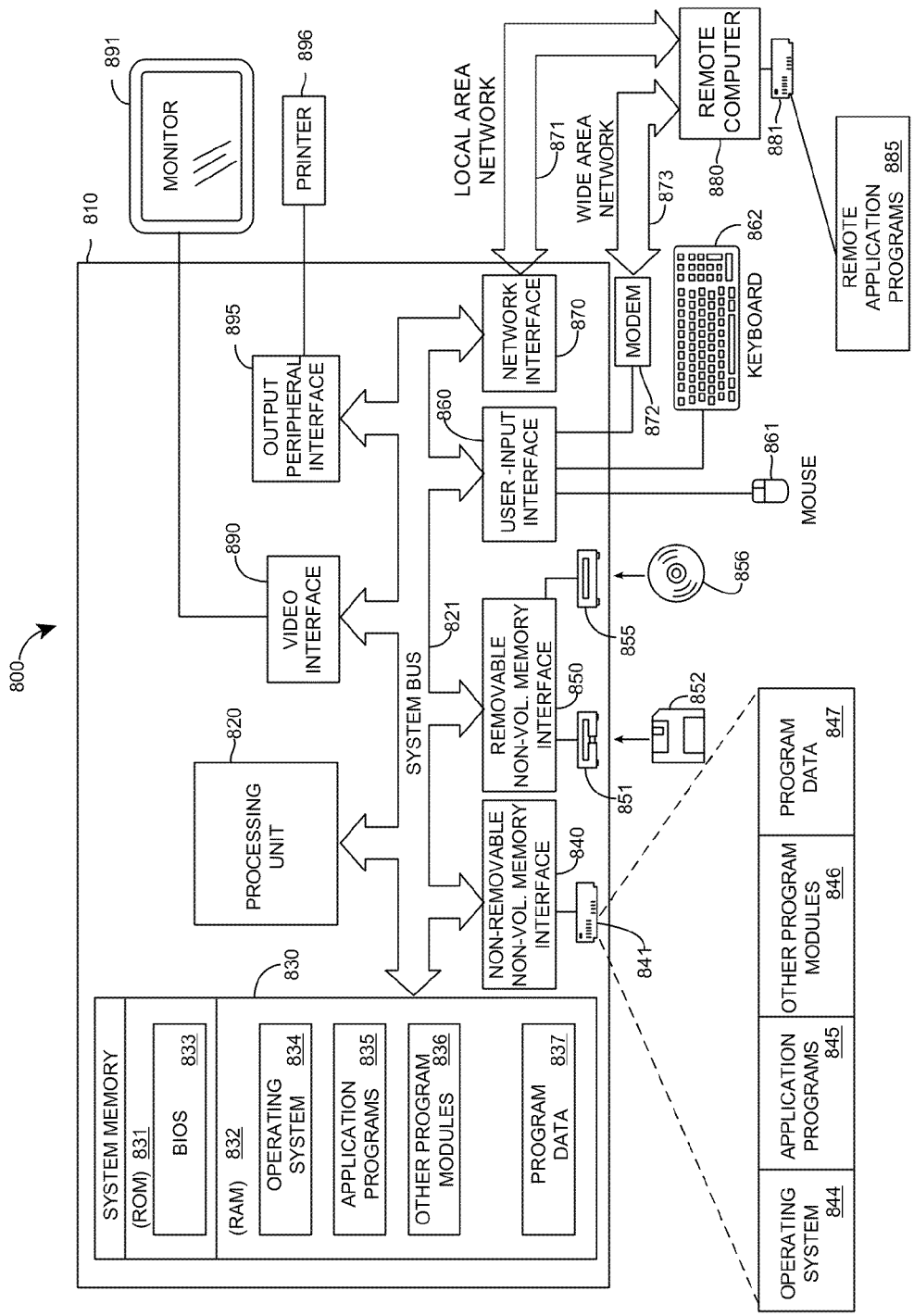
FIG. 10 illustrates an exemplary block diagram of a computer system on which an exemplary personalized health risk assessment system may operate in accordance with the described embodiments.

Health risk assessments may be generated using an electronic system. FIGS. 9 and 10 provide an exemplary structural basis for the network and computational platforms related to such a system.

FIG. 9 illustrates an exemplary block diagram of a network 700 and computer hardware that may be utilized in an exemplary personalized health risk assessment system in accordance with the described embodiments. The network 700 may be the Internet, a virtual private network (VPN), or any other network that allows one or more computers, communication devices, databases, etc., to be communicatively connected to each other. The network 700 may be connected to a personal computer 712, and a computer terminal 714 via an Ethernet 716 and a router 718, and a landline 720. The Ethernet 716 may be a subnet of a larger Internet Protocol network. Other networked resources, such as projectors or printers (not depicted), may also be supported via the Ethernet 716 or another data network. On the other hand, the network 700 may be wirelessly connected to a laptop computer 722 and a personal data assistant 724 via a wireless communication station 726 and a wireless link 728. Similarly, a server 730 may be connected to the network 700 using a communication link 732 and a mainframe 734 may be connected to the network 700 using another communication link 736. The network 700 may be useful for supporting peer-to-peer network traffic.

With respect to the health risk assessment embodiments described above, the training data and/or target data may be received over a network such as the network 700, for example. For example, a computer such as the personal computer 712, laptop computer 722, server 730 or mainframe 734 may receive the training data and/or target data over the network 700. The training data and/or target data may be received over the network 700 from a computer such as the personal computer 712, laptop computer 722, server 730 or mainframe 734, for example. The training data and/or target data may also be received from a remotely-accessible, free-standing memory device on the network 700 (not shown). In some embodiments, the training data and/or target data may be received by more than one computer. In other embodiments, the training data and/or target data may be received from more than one computer and/or remotely-accessible memory device.

Some or all calculations performed in the health risk assessment embodiments described above (e.g., calculations for generating model data or determining whether target data is anomalous) may be performed by a computer such as the personal computer 712, laptop computer 722, server 730 or mainframe 734, for example. In some embodiments, some or all of the calculations may be performed by more than one computer.

Indicating target patient risk, as described above in the health risk assessment embodiments, may also be performed by a computer such as the personal computer 712, laptop computer 722, server 730 or mainframe 734, for example. The indications may be made by setting the value of a data field, for example. In some embodiments, indicating target patient risk may include sending data over a network such as network 700 to another computer.

FIG. 10 illustrates an exemplary block diagram of a computer system 800 on which an exemplary personalized health risk assessment method may operate in accordance with the described embodiments. The computer system 800 of FIG. 10 includes a computing device in the form of a computer 810. Components of the computer 810 may include, but are not limited to, a processing unit 820, a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. By way of example, and not limitation, such architectures include the Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus (also known as Mezzanine bus).

Computer 810 typically includes a variety of computer readable media. Computer readable media can be any available media that can be accessed by computer 810 and includes both volatile and nonvolatile media, and both removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 810. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above are also included within the scope of computer readable media.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 10 illustrates operating system 834, application programs 835, other program modules 836, and program data 837.

The computer 810 may also include other removable/non-removable, volatile/nonvolatile computer storage media. By way of example only, FIG. 10 illustrates a hard disk drive 841 that reads from or writes to non-removable, nonvolatile magnetic media, a magnetic disk drive 851 that reads from or writes to a removable, nonvolatile magnetic disk 852, and an optical disk drive 855 that reads from or writes to a removable, nonvolatile optical disk 856 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 841 is typically connected to the system bus 821 through a non-removable memory interface such as interface 840, and magnetic disk drive 851 and optical disk drive 855 are typically connected to the system bus 821 by a removable memory interface, such as interface 850.

The drives and their associated computer storage media discussed above and illustrated in FIG. 10 provide storage of computer readable instructions, data structures, program modules and other data for the computer 810. In FIG. 10, for example, hard disk drive 841 is illustrated as storing operating system 844, application programs 845, other program modules 846, and program data 847. Note that these components can either be the same as or different from operating system 834, application programs 835, other program modules 836, and program data 837. Operating system 844, application programs 845, other program modules 846, and program data 847 are given different numbers here to illustrate that, at a minimum, they are different copies. A user may enter commands and information into the computer 810 through input devices such as a keyboard 862 and cursor control device 861, commonly referred to as a mouse, trackball or touch pad. A monitor 891 or other type of display device is also connected to the system bus 821 via an interface, such as a graphics controller 890. In addition to the monitor, computers may also include other peripheral output devices such as printer 896, which may be connected through an output peripheral interface 895.

The computer 810 may operate in a networked environment using logical connections to one or more remote computers, such as a remote computer 880. The remote computer 880 may be a personal computer, a server, a router, a network PC, a peer device or other common network node, and typically includes many or all of the elements described above relative to the computer 810, although only a memory storage device 881 has been illustrated in FIG. 10. The logical connections depicted in FIG. 10 include a local area network (LAN) 871 and a wide area network (WAN) 873, but may also include other networks. Such networking environments are commonplace in hospitals, offices, enterprise-wide computer networks, intranets and the Internet.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. The modem 872, which may be internal or external, may be connected to the system bus 821 via the input interface 860, or other appropriate mechanism. In a networked environment, program modules depicted relative to the computer 810, or portions thereof, may be stored in the remote memory storage device 881. By way of example, and not limitation, FIG. 10 illustrates remote application programs 885 as residing on memory device 881.

The communications connections 870, 872 allow the device to communicate with other devices. The communications connections 870, 872 are an example of communication media. The communication media typically embodies computer readable instructions, data structures, program modules or other data in a modulated data signal such as a carrier wave or other transport mechanism and includes any information delivery media: A "modulated data signal" may be a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Computer readable media may include both storage media and communication media.

The methods of the health risk assessment embodiments described above may be implemented in part or in their entirety using one or more computer systems such as the computer system 800 illustrated in FIG. 10. The training data and/or target data may be received by a computer such as the computer 810, for example. The training data and/or target data may be received over a communication medium such as local area network 871 or wide area network 873, via network interface 870 or user-input interface 860, for example. As another example, the training data and/or target data may be received from a remote source such as the remote computer 880 where the data is initially stored on memory device such as the memory storage device 881. As another example, the training data and/or target data may be received from a removable memory source such as the nonvolatile magnetic disk 852 or the nonvolatile optical disk 856. As another example, the training data and/or target data may be received as a result of a human entering data through an input device such as the keyboard 862.

Some or all calculations performed in the health risk assessment embodiments described above (e.g., calculations for generating model data or determining a risk level) may be performed by a computer such as the computer 810, and more specifically may be performed by a processor such as the processing unit 820, for example. In some embodiments, some calculations may be performed by a first computer such as the computer 810 while other calculations may be performed by one or more other computers such as the remote computer 880. The calculations may be performed according to instructions that are part of a program such as the application programs 835, the application programs 845 and/or the remote application programs 885, for example.

Indicating target patient risk, as described above in the health risk assessment embodiments, may also be performed by a computer such as the computer 810. The indications may be made by setting the value of a data field stored in the ROM memory 831 and/or the RAM memory 832, for example. In some embodiments, indicating target patient risk may include sending data over a network such as the local area network 871 or the wide area network 873 to another computer, such as the remote computer 881. In other embodiments, indicating target patient risk may include sending data over a video interface such as the video interface 890 to display information relating to risk on an output device such as the monitor 891 or the printer 896, for example.

We claim:

1. A computer-implemented method of assessing whether a patient is at risk of developing a clinical condition, the method comprising:

receiving from a database training data representing a set of patient-related variables for each of a plurality of patients;

generating model data via a computer based on the received training data;

receiving target data representing the set of patient-related variables for a target patient;

determining via the computer a risk level for the target patient of developing the clinical condition, wherein determining the risk level includes performing one or more calculations involving the received target data and the generated model data; and indicating the risk level of developing the clinical condition, wherein i) when the clinical condition is a mortality condition, the set of patient-related variables consists of between three and ten variables selected from the group consisting of: functional health status prior to surgery, American Society of Anesthesiologists (ASA) classification, preoperative serum albumin, age, presence of disseminated cancer, preoperative blood urea nitrogen (BUN), do-not-resuscitate (DNR) status, emergent versus non-emergent case, work relative value unit, and presence of ascites, and ii) when the clinical condition is a morbidity condition, the set of patient-related variables consists of between three and ten variables selected from the group consisting of: ASA classification, work relative value unit, preoperative serum albumin, emergent versus non-emergent case, functional health status prior to surgery, inpatient versus outpatient case, preoperative systemic sepsis, age, steroid use for chronic condition, and weight.

2. The method of claim 1, wherein receiving the training data from the database includes receiving the training data from a National Surgical Quality Improvement Program (NSQIP) database.

3. The method of claim 1, wherein the clinical condition is a mortality condition.

4. The method of claim 1, wherein the clinical condition is a morbidity condition.

5. A computer-implemented method of assessing whether a patient is at risk of developing a clinical condition, the method comprising:

receiving from a database training data representing a set of patient-related variables for each of a plurality of patients;

generating model data via a computer based on the received training data;

receiving target data representing the set of patient-related variables for a target patient;

determining via the computer a risk level for the target patient of developing the clinical condition, wherein determining the risk level includes performing one or more calculations involving the received target data and the generated model data; and indicating the risk level of developing the clinical condition, wherein i) when the clinical condition is a mortality condition, the set of patient-related variables consists of between three and five variables selected from the group consisting of: functional health status prior to surgery, American Society of Anesthesiologists (ASA) classification, preoperative serum albumin, age, presence of disseminated cancer, preoperative blood urea nitrogen (BUN), do-not-resuscitate (DNR) status, emergent versus non-emergent case, work relative value unit, and presence of ascites, and ii) when the clinical condition is a morbidity condition, the set of patient-related variables consists of between three and five variables selected from the group consisting of: ASA classification, work relative value unit, preoperative serum albumin, emergent versus non-emergent case, functional health status prior to surgery, inpatient versus outpatient case, preoperative systemic sepsis, age, steroid use for chronic condition, and weight.

6. The method of claim 5, wherein receiving the training data from the database includes receiving the training data from a National Surgical Quality Improvement Program (NSQIP) database.

7. The method of claim 5, wherein the clinical condition is a mortality condition.

8. The method of claim 5, wherein the clinical condition is a morbidity condition.

9. A computer-implemented method of assessing whether a patient is at risk of developing a clinical condition, the method comprising:
- receiving from a database training data representing a set of patient-related variables for each of a plurality of patients;
- generating model data via a computer based on the received training data;
- receiving target data representing the set of patient-related variables for a target patient;
- determining via the computer a risk level for the target patient of developing the clinical condition, wherein determining the risk level includes performing one or more calculations involving the received target data and the generated model data; and
- indicating the risk level of developing the clinical condition, wherein
  - i) when the clinical condition is a mortality condition, the set of patient-related variables consists of between three and five variables selected from the group consisting of: functional health status prior to surgery, American Society of Anesthesiologists (ASA) classification, preoperative serum albumin, age, and presence of disseminated cancer, and
  - ii) when the clinical condition is a morbidity condition, the set of patient-related variables consists of between three and five variables selected from the group consisting of: ASA classification, work relative value unit, preoperative serum albumin, emergent versus non-emergent case, and functional health status prior to surgery.

10. The method of claim 9, wherein receiving the training data from the database includes receiving the training data from a National Surgical Quality Improvement Program (NSQIP) database.

11. The method of claim 9, wherein the clinical condition is a mortality condition.

12. The method of claim 9, wherein the clinical condition is a morbidity condition.

13. A non-transitory computer-readable storage medium comprising computer-readable instructions to be executed on a processor of a system for assessing whether a patient is at risk of developing a clinical condition, the instructions when executed cause the processor to:
- receive training data from a database representing a set of patient-related variables for each of a plurality of patients;
- generate model data based on the received training data;
- receive target data representing the set of patient-related variables for a target patient;
- automatically determine a risk level for the target patient of developing the clinical condition, wherein determining the risk level includes causing the processor to perform one or more calculations involving the received target data and the generated model data; and
- automatically indicate the risk level of developing the clinical condition, wherein
  - i) when the clinical condition is a mortality condition, the set of patient-related variables consists of between three and ten variables selected from the group consisting of: functional health status prior to surgery, American Society of Anesthesiologists (ASA) classification, preoperative serum albumin, age, presence of disseminated cancer, preoperative blood urea nitrogen (BUN), do-not-resuscitate (DNR) status, emergent versus non-emergent case, work relative value unit, and presence of ascites, and
  - ii) when the clinical condition is a morbidity condition, the set of patient-related variables consists of between three and ten variables selected from the group consisting of: ASA classification, work relative value unit, preoperative serum albumin, emergent versus non-emergent case, functional health status prior to surgery, inpatient versus outpatient case, preoperative systemic sepsis, age, steroid use for chronic condition, and weight.

* * * * *